(12) United States Patent
Han et al.

(10) Patent No.: US 11,259,815 B2
(45) Date of Patent: Mar. 1, 2022

(54) END EFFECTOR INSTRUMENT, END EFFECTOR DEVICE, DELIVERY DEVICE, AND ASSEMBLY BOX

(71) Applicant: HANGZHOU AGS MEDTECH CO., LTD., Zhejiang (CN)

(72) Inventors: Mei Han, Hangzhou (CN); Xiangsen Kong, Hangzhou (CN); Baiming Shi, Hangzhou (CN)

(73) Assignee: HANGZHOU AGS MEDTECH CO., LTD., Hangzhou (CN)

( * ) Notice: Subject to any disclaimer, the term of this patent is extended or adjusted under 35 U.S.C. 154(b) by 159 days.

(21) Appl. No.: 16/609,794

(22) PCT Filed: May 4, 2017

(86) PCT No.: PCT/CN2017/083092
§ 371 (c)(1),
(2) Date: Oct. 31, 2019

(87) PCT Pub. No.: WO2018/201406
PCT Pub. Date: Nov. 8, 2018

(65) Prior Publication Data
US 2020/0060685 A1 Feb. 27, 2020

(51) Int. Cl.
*A61B 17/128* (2006.01)
*A61B 17/122* (2006.01)
(Continued)

(52) U.S. Cl.
CPC ...... *A61B 17/1285* (2013.01); *A61B 17/1222* (2013.01); *A61B 17/1227* (2013.01);
(Continued)

(58) Field of Classification Search
CPC .............. A61B 17/122; A61B 17/1222; A61B 17/1227; A61B 17/128; A61B 17/1285
See application file for complete search history.

(56) References Cited

U.S. PATENT DOCUMENTS 5,797,939 A 8/1998 Yoon
7,488,334 B2* 2/2009 Jugenheimer ........ A61B 17/122
606/142
(Continued)

FOREIGN PATENT DOCUMENTS

CN 202477780 U 10/2012
CN 202699217 U 1/2013
(Continued)

OTHER PUBLICATIONS

International Search Report in PCT/CN2017/083092 dated Feb. 8, 2018, 8 pages.
(Continued)

*Primary Examiner* — Ryan J. Severson
(74) *Attorney, Agent, or Firm* — Metis IP LLC

(57) ABSTRACT

The present disclosure relates to an end effector instrument. The end effector instrument may include an end effector device. The end effector device may include a clip and a resilient portion including a connecting hole and a limiting convex. The end effector instrument may further include a delivery device including a sheath and a shaft. The sheath may include a passage that accommodates the shaft. A distal end of the shaft may include a connecting end. The sheath may include a limiting concave. The connecting end may extend into or exit from the connecting hole when the sheath is set outside the resilient portion: when the connecting end extends into the connecting hole, the resilient portion may expand outward, and the limiting convex may extend into the limiting concave; when the connecting end exits from the connecting hole, the resilient portion may rebound, and the limiting convex may exit from the limiting concave. The end effector device may be operated repeatedly, and the delivery device may be reused.

18 Claims, 43 Drawing Sheets

(51) Int. Cl.
*A61B 17/00* (2006.01)
*A61B 17/12* (2006.01)

(52) U.S. Cl.
CPC ............... *A61B 2017/00477* (2013.01); *A61B 2017/12004* (2013.01)

(56) References Cited

U.S. PATENT DOCUMENTS

| | | | | |
|---|---|---|---|---|
| 7,727,247 | B2* | 6/2010 | Kimura | A61B 50/30 606/157 |
| 8,157,824 | B2* | 4/2012 | Kimura | A61B 17/1222 606/157 |
| 8,348,964 | B2* | 1/2013 | Kimura | A61B 17/1222 606/157 |
| 8,465,501 | B2* | 6/2013 | Matsuoka | A61B 17/1227 606/142 |
| 8,480,685 | B2* | 7/2013 | Kimura | A61B 17/122 606/139 |
| 8,551,119 | B2* | 10/2013 | Kogiso | A61B 17/1227 606/142 |
| 8,668,707 | B2* | 3/2014 | Thompson | A61B 17/12104 606/157 |
| 8,690,899 | B2* | 4/2014 | Kogiso | A61B 17/1285 606/151 |
| 9,138,234 | B2* | 9/2015 | Li | A61B 17/122 |
| 9,492,176 | B2* | 11/2016 | Zhu | A61B 17/1285 |
| 9,510,836 | B2* | 12/2016 | Zhu | A61B 17/122 |
| 9,743,933 | B2* | 8/2017 | Phillips-Hungerford | A61B 17/1285 |
| 9,980,725 | B2* | 5/2018 | Durgin | A61B 17/122 |
| 10,010,323 | B2* | 7/2018 | Barner | A61B 17/122 |
| 10,143,479 | B2* | 12/2018 | Adams | A61B 17/1285 |
| 10,172,623 | B2* | 1/2019 | Adams | A61B 17/1285 |
| 10,172,624 | B2* | 1/2019 | Adams | A61B 17/122 |
| 10,335,159 | B2* | 7/2019 | Naveed | A61B 17/0057 |
| 10,441,292 | B2* | 10/2019 | Tsueda | A61B 17/122 |
| 10,470,775 | B2* | 11/2019 | Shi | A61B 17/1227 |
| 10,492,794 | B2* | 12/2019 | Ikeda | A61B 17/122 |
| 10,524,786 | B2* | 1/2020 | Khan | A61B 17/1285 |
| 10,624,642 | B2* | 4/2020 | Randhawa | A61B 17/105 |
| 10,646,228 | B2* | 5/2020 | Hayashi | A61B 17/1285 |
| 11,020,125 | B2* | 6/2021 | Randhawa | A61B 17/1285 |
| 11,045,194 | B2* | 6/2021 | King | A61B 17/12009 |
| 2004/0097982 | A1 | 5/2004 | Jugenheimer et al. | |
| 2005/0143767 | A1* | 6/2005 | Kimura | A61B 17/1222 606/158 |
| 2007/0112359 | A1 | 5/2007 | Kimura et al. | |
| 2008/0140089 | A1 | 6/2008 | Kogiso et al. | |
| 2010/0217292 | A1 | 8/2010 | Kimura et al. | |
| 2010/0217293 | A1* | 8/2010 | Kimura | A61B 17/1222 606/157 |
| 2011/0196390 | A1* | 8/2011 | Kogiso | A61B 17/122 606/151 |
| 2011/0245855 | A1 | 10/2011 | Matsuoka et al. | |
| 2012/0065646 | A1 | 3/2012 | Phillips-Hungerford et al. | |
| 2013/0102887 | A1 | 4/2013 | Thompson et al. | |
| 2013/0123818 | A1* | 5/2013 | Li | A61B 17/122 606/157 |
| 2014/0088616 | A1 | 3/2014 | Clerc et al. | |
| 2014/0171973 | A1 | 6/2014 | Zhu | |
| 2014/0171974 | A1 | 6/2014 | Zhu | |
| 2015/0190136 | A1 | 7/2015 | Cohen et al. | |
| 2015/0245838 | A1 | 9/2015 | Barner et al. | |
| 2016/0128698 | A1 | 5/2016 | Adams et al. | |
| 2016/0143644 | A1 | 5/2016 | Adams et al. | |
| 2016/0213378 | A1 | 7/2016 | Adams et al. | |
| 2016/0242778 | A1 | 8/2016 | Xu et al. | |
| 2016/0262748 | A1 | 9/2016 | Durgin et al. | |
| 2017/0020531 | A1 | 1/2017 | Naveed et al. | |
| 2017/0086824 | A1 | 3/2017 | Khan | |
| 2017/0296197 | A1 | 10/2017 | Tsueda et al. | |
| 2017/0325823 | A1* | 11/2017 | Phillips-Hungerford | A61B 17/1285 |
| 2018/0049745 | A1 | 2/2018 | Randhawa et al. | |
| 2018/0140300 | A1 | 5/2018 | Randhawa | |
| 2018/0153552 | A1 | 6/2018 | King et al. | |
| 2018/0333156 | A1 | 11/2018 | Hayashi et al. | |
| 2018/0344323 | A1 | 12/2018 | Shi | |
| 2019/0046205 | A1 | 2/2019 | Ikeda et al. | |
| 2019/0216466 | A1 | 7/2019 | Mathis et al. | |
| 2020/0060685 | A1* | 2/2020 | Han | A61B 17/1285 |
| 2020/0113573 | A1* | 4/2020 | Shi | A61B 17/122 |

FOREIGN PATENT DOCUMENTS

| | | |
|---|---|---|
| CN | 106419992 A | 2/2017 |
| JP | 2004073646 A | 3/2004 |
| JP | 2009125548 A | 6/2009 |

OTHER PUBLICATIONS

The Partial Supplementary Search Report in European Application No. 17908447.0 dated Mar. 26, 2020, 12 pages.

* cited by examiner

US 11,259,815 B2

END EFFECTOR INSTRUMENT, END EFFECTOR DEVICE, DELIVERY DEVICE, AND ASSEMBLY BOX

CROSS-REFERENCE TO RELATED APPLICATIONS

The present application is a U.S. national stage under 35 U.S.C. § 371 of International Application No. PCT/CN2017/083092, filed on May 4, 2017, designating the United States of America, the entire contents of which are incorporated herein by reference.

TECHNICAL FIELD

The present disclosure relates to medical devices, and more particularly, relates to an end effector instrument, an end effector device, a delivery device, and an assembly box.

BACKGROUND

Clinically, a treatment is performed using a mechanical compression method for hemostasis, which is achieved using an endoscope with a clip. End effector devices currently used in clinical practice include a device part with a split clip (also referred to as "split type end effector device"), or a device part integrated with a clip (also referred to as "integrated type end effector device").

The clip of the split type end effector device is disposable, and the device part is reused, thereby saving cost, reducing medical waste, and being economical and environmentally friendly. However, the split type end effector device used in clinical practice is not easy to be operated during use. The clip cannot be reopened once it is closed, and cannot be repeatedly opened and closed. The integrated type end effector device can be repeatedly opened and closed. While the clip and the device part are both disposable, which increases the cost and causes underestimated medical waste.

Therefore, there is an urgent need for an end effector device capable of opening and closing repeatedly, with low cost, with a reusable device part, and achieving a quick and safe installation of the clip and the device part.

SUMMARY

In view of the above-mentioned facts, in order to overcome the defects of the prior arts, an end effector instrument, an end effector device, a delivery device, and an assembly box are provided in the present disclosure. A clip of the end effector device may be repeatedly operated and the delivery device may be reused.

Technical solutions of the present disclosure may include:

An end effector instrument may include an end effector device. The end effector device may include a clip and a resilient portion having a connecting hole and a limiting convex. The end effector instrument may further include a delivery device including a sheath and a shaft. The sheath may provide a passage that accommodates the shaft. A distal end of the shaft may include a connecting end. The sheath may include a limiting concave. The connecting end may extend into or exit from the connecting hole when the sheath is arranged outside the resilient portion. When the connecting end extends into the connecting hole, the resilient portion may expand laterally outward, and the limiting convex may extend into the limiting concave. When the connecting end exits from the connecting hole, the resilient portion may extend laterally inward, and the limiting convex may exit from the limiting concave.

In some embodiments, there may be at least two limiting convexes.

In some embodiments, the end effector device may further include a connecting pipe. The clip may be mounted on the connecting pipe, and the connecting pipe may have a channel. The resilient portion may include an elastic ring disposed in the channel of the connecting pipe. The elastic ring may include the connecting hole and the limiting convex. The connecting hole may be connected to the channel of the connecting pipe, and a pipe wall of the connecting pipe may have a limiting hole corresponding to the limiting convex.

In some embodiments, the elastic ring may include a notch.

In some embodiments, a proximal end of the clip may extend into the channel of the connecting pipe. The proximal end of the clip may have a clamping hole connected to the channel of the connecting pipe. A distal end of the connecting end may have a clamping portion matched with the clamping hole. The clamping portion may include a recessed portion and an expanded portion. The recessed portion may be located between the expanded portion and the connecting end. The maximum width of the expanded portion may be greater than the minimum width of the recessed portion, and may be greater than the minimum width of the clamping hole.

In some embodiments, a distal end of the expanded portion may have a guide portion. The cross-section of the guide portion may gradually decrease from its proximal end to its distal end.

In some embodiments, the clip may include at least two clip arms. The proximal end of each clip arm may have a tail clamp. There may be a space between at least two of the tail clamps, which may form the clamping hole.

In some embodiments, the end effector device may further include a connecting pipe. The clip may be mounted on the connecting pipe. The connecting pipe may include a channel. The resilient portion may include a half-ring located in the channel of the connecting pipe. The limiting convex may be set on one side of the half-ring. The connecting hole may be formed between the other side of the half-ring and an inner wall of the connecting pipe.

In some embodiments, a side of the limiting convex may include a limiting portion set in the channel of the connecting pipe.

In some embodiments, the elastic ring may include at least two half-rings. At least two of the half-rings may form the connecting hole, and the half-rings may have the limiting convex.

An end effector instrument may include an end effector device. The end effector device may include a connecting pipe and a clip mounted on the connecting pipe. The connecting pipe may include a channel, and an inner wall of the connecting pipe may have a limiting concave. The end effector instrument may further include a delivery device including a sheath and a shaft. The sheath may provide a passage that accommodates the shaft. A distal end of the shaft may include a connecting end. A distal end of the sheath may include a resilient portion. The resilient portion may have a connecting hole connected to the passage of the sheath. The resilient portion may include a limiting convex. The connecting end may extend into or exit from the connecting hole when the resilient portion extends into the channel of the connecting pipe. When the connecting end extends into the connecting hole, the resilient portion may be pushed to expand outward, and the limiting convex may extend into the limiting concave. When the connecting end exit from the connecting hole, the resilient portion may extend inward, and the limiting convex may exit from the limiting concave.

In some embodiments, there may be at least two limiting convexes.

In some embodiments, the resilient portion may include an elastic ring located at a distal end of the sheath. The elastic ring may be positioned in the passage of the sheath, and include the connecting hole and the limiting convex. A pipe wall of the sheath may have a limiting hole corresponding to the limiting convex.

In some embodiments, the elastic ring may include a notch.

In some embodiments, a proximal end of the clip may extend into the channel of the connecting pipe. The proximal end of the clip may include a clamping hole connected to the channel of the connecting pipe. A distal end of the connecting end may have a clamping portion matched with the clamping hole. The clamping portion may include a recessed portion and an expanded portion. The recessed portion may be located between the expanded portion and the connecting end. The maximum width of the expanded portion may be greater than the minimum width of the recessed portion, and greater than the minimum width of the clamping hole.

In some embodiments, a distal end of the expanded portion may have a guide portion. The cross-section of the guide portion may gradually decrease from its proximal end to its distal end.

In some embodiments, the clip may include at least two clip arms. The proximal end of each clip arm may include a tail clamp. There may be a space between at least two of the tail clamps, which may form the clamping hole.

In some embodiments, the resilient portion may include a half-ring set in the channel of the connecting pipe. The limiting convex may be set on one side of the half-ring. The connecting hole may be formed between the other side of the half-ring and an inner wall of the connecting pipe.

In some embodiments, a side of the limiting convex may include a limiting portion set in the channel of the connecting pipe.

In some embodiments, the elastic ring may include at least two half-rings. At least two of the half-rings may form the connecting hole, and the half-rings may include the limiting convex.

An end effector device may include a clip and a resilient portion connected with the clip. The resilient portion may include a connecting hole and a limiting convex. The resilient portion may expand outward when the resilient portion is subjected to a force applied from the connecting hole. The resilient portion may expand inward when the force applied from the connecting hole on the resilient portion is withdrawn.

In some embodiments, there may be at least two limiting convexes.

In some embodiments, the end effector device may further include a connecting pipe. The clip may be mounted on the connecting pipe, and the connecting pipe may include a passage. The resilient portion may include an elastic ring set in the passage of the connecting pipe. The elastic ring may include the connecting hole and the limiting convex. The connecting hole may be connected to the channel of the connecting pipe, and a pipe wall of the connecting pipe may include a limiting hole corresponding to the limiting convex.

In some embodiments, the elastic ring may include a notch.

In some embodiments, a proximal end of the clip may extend into the channel of the connecting pipe. The proximal end of the clip may include a clamping hole connected to the channel of the connecting pipe.

In some embodiments, the clip may include at least two clip arms. The proximal end of each clip arm may include a tail clamp. There may be a space between at least two of the tail clamps, which may form the clamping hole.

In some embodiments, the end effector device may further include a connecting pipe. The clip may be mounted on the connecting pipe. The connecting pipe may include a channel. The resilient portion may include a half-ring. The limiting convex may be set on one side of the half-ring. The connecting hole may be formed between the other side of the half-ring and an inner wall of the connecting pipe.

In some embodiments, a side of the limiting convex may include a limiting portion set in the channel of the connecting pipe.

In some embodiments, the elastic ring may include at least two half-rings. At least two of the half-rings may form the connecting hole, and the half-rings may include the limiting convex.

An end effector device may include a connecting pipe and a clip mounted on the connecting pipe. The connecting pipe may include a channel. An inner wall of the connecting pipe may have a limiting concave.

In some embodiments, a proximal end of the clip may extend into the channel of the connecting pipe. The proximal end of the clip may include a clamping hole connected to the channel of the connecting pipe.

In some embodiments, the clip may include at least two clip arms. The proximal end of each clip arm may include a tail clamp. There may be a space between at least two of the tail clamps, which may form the clamping hole.

In some embodiments, the resilient portion may include a half-ring set in the channel of the connecting pipe. The limiting convex may be set on one side of the half-ring. The connecting hole may be formed between the other side of the half-ring and an inner wall of the connecting pipe.

A delivery device may include a sheath and a shaft. The sheath may include a passage that accommodates the shaft. A distal end of the shaft may include a connecting end. An inner wall of the sheath may include a limiting concave.

In some embodiments, a distal end of the connecting end may include a clamping portion including a recessed portion and an expanded portion. The recessed portion may be located between the expanded portion and the connecting end. The maximum width of the expanded portion may be greater than the minimum width of the recessed portion.

In some embodiments, a distal end of the expanded portion may include a guide portion. The cross-section of the guide portion may gradually decrease from its proximal end to its distal end.

A delivery device may include a sheath and a shaft. The sheath may include a passage that accommodates the shaft. A distal end of the shaft may include a connecting end. A distal end of the sheath may include a resilient portion. The resilient portion may include a connecting hole connected to the passage of the sheath. The resilient portion may include a limiting convex. The connecting end may extend into or exit from the connecting hole. When the connecting end extends into the connecting hole, the resilient portion may expand laterally outward. When the connecting end exit from the connecting hole, the resilient portion may extend laterally inward.

In some embodiments, a pipe wall of the sheath may include a limiting hole. The resilient portion may include an elastic ring set in the passage of the sheath. The elastic ring may include the connecting hole and the limiting convex. The limiting hole may correspond to the limiting convex.

In some embodiments, a distal end of the connecting end may include a clamping portion including a recessed portion and an expanded portion. The recessed portion may be located between the expanded portion and the connecting end. The maximum width of the expanded portion may be greater than the minimum width of the recessed portion.

In some embodiments, a distal end of the expanded portion may include a guide portion. The cross-section of the guide portion may gradually decrease from its proximal end to its distal end.

In some embodiments, a side of the limiting convex may include a limiting portion set in the channel of the connecting pipe.

In some embodiments, there may be at least two limiting convexes.

In some embodiments, the elastic ring may include a notch.

In some embodiments, the elastic ring may include at least two half-rings. At least two of the half-rings may form the connecting hole, and the half-rings may include the limiting convex.

An assembly box for assembling the end effector device with the delivery device may include a body. The body may include a chamber form accommodating an end effector device and a chamber for accommodating a sheath. The chamber for accommodating the end effector device may be configured to accommodate the end effector device. The chamber for accommodating the sheath may be configured to accommodate the sheath. One end of the chamber for accommodating the sheath may be connected to the chamber for accommodating the end effector device, and the other end of the chamber for accommodating the sheath may include an opening.

In some embodiments, the chamber for accommodating the end effector device may include a chamber for accommodating a clip and a chamber for accommodating a connecting pipe connected to the chamber for accommodating the clip. The chamber for accommodating the clip may be configured to accommodate the clip, and the chamber for accommodating the connecting pipe may be configured to accommodate the connecting pipe.

In some embodiments, a positioning convex may be located between the chamber for accommodating the clip and the chamber for accommodating the connecting pipe. The positioning convex may be configured to abut a distal end of the connecting pipe.

In some embodiments, the chamber for accommodating the clip may accommodate the clip in an open state.

In some embodiments, the body may include an accommodating section and a clamping section connected to each other. The accommodating section may include the chamber for accommodating the end effector device. The clamping section may include the chamber for accommodating the sheath. The chamber for accommodating the sheath may be deformed for clamping the sheath when the clamping section is subjected to an extrusion force.

In some embodiments, the clamping section may include at least two clamping pieces. At least two of the clamping pieces may form the chamber for accommodating the sheath. When the clamping pieces are subjected to an extrusion force, at least two of the clamping pieces may be moved towards each other for clamping the sheath.

The beneficial effects of the present disclosure may include:

The first group: articles 1 to 10 are described as the first group of schemes.

1. An end effector instrument may include an end effector device and a delivery device. The end effector device may include a clip and a resilient portion having a connecting hole. An outer peripheral surface of the resilient portion may include a limiting convex. The clip may be used for ligation.

The delivery device may include a sheath and a shaft. The sheath may include a passage that accommodates the shaft. The shaft may be movable relative to the sheath between a proximal end or a distal end. As used herein, that along the longitudinal direction of the end effector instrument (the delivery device may be of a long-lined shape in general as the end effector device is sent to the human body through the delivery device for ligation) or along the direction in which the end effector instrument enters into the human body, the end facing an operator may be referred to as the "proximal end", and the end facing the human body for treatment may be referred to as the "distal end". The "proximal end" may include an end face of the proximal end and a part near the end face of the proximal end. The "distal end" may include an end face of the distal end and a part near the end face of the distal end. The "proximal end" of a component may refer to the side of the component facing the operator, and the "distal end" of the component may refer to the side of the component extending towards the human body for treatment. The "proximal end" of the component may include an end face of the proximal end and a part near the end face of the proximal end. The "distal end" of the component may include an end face of the distal end and a part near the end face of the distal end.

An inner wall of the sheath may include a limiting concave. The resilient portion may be matched with the limiting concave for connecting the end effector device and the delivery device. The connecting end may extend into or exit from the connecting hole when the sheath is set outside the resilient portion. When the connecting end extends into the connecting hole, the resilient portion may expand outward, and the limiting convex may extend into the limiting concave. At this time, the limiting convex may be limited by the limiting concave, and the sheath may be connected with the end effector device. When the connecting end exits from the connecting hole, the resilient portion may rebound, the limiting convex may exit from the limiting concave, and the connection between the sheath and the end effector device may be released.

The connecting end may extend into or exit from the connecting hole, which may connect the sheath with the end effector device, or relieve the connection between the sheath and the end effector device. As long as the delivery device is configured with a connecting end matching with the resilient portion(s), the delivery device may be used in connection with a plurality of end effector devices, such that the delivery device may be reused. Different delivery devices may be used for end effector devices of the same type, which may greatly improve the applicability and versatility of the end effector instrument.

The elasticity of the resilient portion may be used to rebound the resilient portion and cause the limiting convex to exit from the limiting concave after the connecting end exits from the connecting hole, thereby releasing the connection between the end effector device and the sheath. The material of the resilient portion may not be limited to elastic materials or non-elastic materials, as long as the resilient portion may rebound and the limiting convex may exit from the limiting concave.

2. There may be at least two limiting convexes. And there may be one limiting concave, or a plurality of limiting concaves matching the limiting convexes. Each limiting convex may extend into a corresponding limiting concave to form a plurality of connection points, which may make the connection between the end effector device and the sheath more stable. Preferably, the plurality of limiting convexes may be symmetrically arranged to make it evenly stressed.

3. The end effector device may further include a connecting pipe. The clip may be mounted on the connecting pipe, and the connecting pipe may include a channel. The resilient portion may include an elastic ring set in the channel of the connecting pipe. The elastic ring may include the connecting hole and the limiting convex. The connecting hole may be connected to the channel of the connecting pipe, and a pipe wall of the connecting pipe may include a limiting hole corresponding to the limiting convex.

When the sheath is set outside the connecting pipe, the sheath may be located outside the elastic ring. When the shaft is pushed toward the distal end, the connecting end may be driven to move toward the distal end and extend into the connecting hole, the elastic ring may expand outward, such that the limiting convex may extend through the limiting hole and further into the limiting concave, and the connecting pipe may be connected with the sheath.

4. The elastic ring may include a notch. The notch may increase the degree of expansion of the elastic ring as it is extruded, such that the connection between the limiting convex and the limiting concave may be stable. At the same time, it may also cause the connecting end to be inserted into the connecting hole more easily.

5. A proximal end of the clip may extend into the channel of the connecting pipe. The proximal end of the clip may include a clamping hole connected to the channel of the connecting pipe. A distal end of the connecting end may include a clamping portion matched with the clamping hole. The clamping portion may include a recessed portion and an expanded portion. The recessed portion may be located between the expanded portion and the connecting end. The maximum width of the expanded portion may be greater than the minimum width of the recessed portion, and greater than the minimum width of the clamping hole.

The maximum width of the expanded portion may refer to the maximum width of its cross-section. For example, if the expanded portion is a cylinder with a circular cross-section, the maximum width of the expanded portion may be the diameter of the circle. If the cross-section of the expanded portion is a rectangle, the maximum width of the expanded portion may be the length of the diagonal of the rectangle.

The maximum width of the expanded portion may be greater than the maximum width of the recessed portion so that the expanded portion and the recessed portion may form a "step". When the expanded portion is pushed to move to the distal end so that the expanded portion passes through the clamping hole, the clamping hole may buckle in the recessed portion, and a connection between the connecting end and the clip may be accomplished. At this point, the clip may be driven to move towards the distal end when the shaft is pushed to the distal end. When the clip extends out of the connecting pipe long enough, the clip may open. The clip may be driven to the proximal end when the shaft is pulled towards the proximal end. When the clip enters the channel of the connecting pipe long enough, the clip may be closed.

After the clip is closed, continuing to pull the shaft to the proximal end may drive the clip to move to the proximal end. When the clamping portion exits from the clamping hole, the connection between the clip and the shaft may be released. Edges of the clamping hole may be deformed, broken, or ruptured by the expanded portion. At this time, a separation of the connecting end and the clip may be realized, which may not affect the actual use.

Preferably, by using a suitable shape and diameter of the clamping hole, a suitable shape and width of the expanded portion, and materials surrounding the clamping hole, the expanded portion and the clamping hole may be repeatedly buckled or connected without loss.

6. A distal end of the expanded portion may include a guide portion. The cross-section of the guide portion may gradually decrease from its proximal end to its distal end. The cross-section of the guide portion may refer to a cross-section of the guide portion in a direction that is perpendicular or approximately perpendicular to the moving direction of the expanded portion towards the distal end. The cross-section of the guide portion may gradually decrease such that a guiding slope may be formed on an outer surface of the guide portion, which may guide the expanded portion to extend into the clamping hole more smoothly.

7. The clip may include at least two clip arms. The proximal end of each clip arm may include a tail clamp. There may be a space between at least two of the tail clamps, which may form the clamping hole. The clamping hole may be formed by the clip arms, thereby having a simple structure. In general, the clip arms may be flat pieces. Preferably, the proximal ends of the clip arms may be bent in a direction perpendicular or nearly perpendicular to the flat surface and form L hooks. A space between the L hooks of the two clip arms may form the clamping hole. The L hooks of the two clip arms may be symmetrically arranged with respect to the clamping hole, and the L hooks of the two clip arms may be edges of the clamping hole. In this way, the clamping hole may be formed on flat clip arms, which may have a simple structure and may be manufactured with a high production efficiency.

8. The clip may further include a connecting pin. The proximal ends of the clip arms may include a locking convex and a connecting hole. The connecting pin may be set through the connecting hole. When at least two clip arms are guided by the connecting pipe to be closed, the proximal ends of the at least two clip arms may slide along the connecting pin and bounce away from each other, and the locking convex may extend into a locking concave. When the proximal ends of the clip arms are close to the distal end of the connecting pipe, the distal ends of the clip arms may be far apart from each other, and the clip arms may open. When the proximal ends of the clip arms are moved towards to the proximal end of the connecting pipe, the distal ends of the clip arms may be guided by the connecting pipe to be closed, the proximal ends of the clip arms may be moved away from each other, and the locking convex may extend into the locking concave, thereby the clip arms may be locked in the connecting pipe, thus preventing the clip arms from moving relative to the connecting pipe, keeping the clip arms closed, and preventing the clip from loosening after a ligation.

Preferably, the clip arms may include curvatures that allow the clip arms to automatically open or close.

Preferably, the distal end of the connecting pipe may include a blocking portion between the two clip arms. The blocking portion may block the connecting pin to prevent the clip arms from moving out of the opening of the connecting pipe at the distal end.

9. The side of the limiting convex may include a limiting portion set in the channel of the connecting pipe. When the resilient portion is extruded and expands outward, the limiting portion may abut an outer side of the limiting concave, or may abut the limiting hole, so as to prevent the resilient portion from stretching excessively.

10. The elastic ring may be comprised of at least two half-rings that forms a connecting hole. The half-ring may include a limiting convex. The half-ring may be set directly in the channel of the connecting pipe to align the limiting convex with the limiting hole. The half-ring may be a ½ ring, a ⅓ ring, or a ring of other shapes, as long as it may automatically rebound when the connecting end exits from the connecting hole, such that the connection between the end effector device and the sheath may be released.

The second group: articles 11 to 12 are described as the second group of schemes.

11. An end effector instrument may be similar to that described in the first group. However, the difference is that the end effector instrument may include an end effector device and a delivery device.

The end effector device may include a connecting pipe and a clip mounted on the connecting pipe. The clip may be used for ligation. The connecting pipe may include a channel, and an inner wall of the connecting pipe may have a limiting concave.

The delivery device may include a sheath and a shaft. The sheath may include a passage that accommodates the shaft. A distal end of the shaft may include a connecting end. A distal end of the sheath may include a resilient portion. The resilient portion may include a connecting hole connected to the passage of the sheath. An outer peripheral surface of the resilient portion may include a limiting convex.

The connecting end may extend into or exit from the connecting hole when the resilient portion extends into the channel of the connecting pipe. When the connecting end extends into the connecting hole, the resilient portion may be extruded to expand outward, and the limiting convex may extend into the limiting concave. When the connecting end exit from the connecting hole, the resilient portion may rebound, and the limiting convex may exit from the limiting concave. The connecting end extending into or exiting from the connecting hole may connect the sheath with the connecting pipe, or release the connection between the sheath and the connecting pipe. As long as a matching connecting pipe, a matching resilient portion, and a matching connecting end are used in the end effector device and the delivery device, one delivery device may be used in connection with a plurality of end effector devices, and the delivery device may be reused. Different delivery devices may also be used with the end effector devices in the same type, which may greatly improve the applicability and versatility of the end effector instrument.

The elasticity of the resilient portion may be used to rebound the resilient portion and cause the limiting convex to exit from the limiting concave after the connecting end exits from the connecting hole, thereby releasing the connection between the end effector device and the sheath. The material of the resilient portion may not be limited to elastic materials or non-elastic materials, as long as the resilient portion may rebound and the limiting convex may exit from the limiting concave.

12. There may be at least two limiting convexes. And there may be one limiting concave, or a plurality of limiting concaves matching the limiting convexes. Each limiting convex may extend into a corresponding limiting concave to form a plurality of connection points, which may make the connection between the end effector device and the sheath more stable. Preferably, the plurality of limiting convexes may be symmetrically arranged to make it evenly stressed.

13. The distal end of the sheath may include an elastic ring. The elastic ring may be set in a passage of the sheath as a resilient portion. The elastic ring may include a connecting hole and a limiting convex. A pipe wall of the sheath may include a limiting hole corresponding to the limiting convex. When the resilient portion extends into the connecting pipe, the connecting pipe may be set outside the elastic ring. When the shaft is pushed toward the distal end of the connecting pipe, the connecting end may be driven to move towards the distal end and extend into the connecting hole, the elastic ring may expand outward, such that the limiting convex may extend through the limiting hole and further into the limiting concave, and thus the connecting pipe may be connected to the sheath.

14. The elastic ring may include a notch. The notch may increase the degree of expansion of the elastic ring as it is extruded, such that the connection between the limiting convex and the limiting concave may be stable. At the same time, it may also cause the connecting end to be inserted into the connecting hole more easily.

15. A proximal end of the clip may extend into the channel of the connecting pipe. The proximal end of the clip may include a clamping hole connected to the channel of the connecting pipe. A distal end of the connecting end may include a clamping portion matched with the clamping hole. The clamping portion may include a recessed portion and an expanded portion. The recessed portion may be located between the expanded portion and the connecting end. The maximum width of the expanded portion may be greater than the minimum width of the recessed portion, and greater than the minimum width of the clamping hole. As used herein, the maximum width of the expanded portion may refer to the maximum width of its cross-section. For example, if the expanded portion is a cylinder with a circular cross-section, the maximum width of the expanded portion may be the diameter of the circle. If the cross-section of the expanded portion is a rectangle, the maximum width of the expanded portion may be the length of the diagonal of the rectangle.

The maximum width of the expanded portion may be greater than the maximum width of the recessed portion so that the expanded portion and the recessed portion may form a "step". When the expanded portion is pushed to move to the distal end so that the expanded portion passes through the clamping hole, the clamping hole may buckle in the recessed portion, and a connection between the connecting end and the clip may be accomplished. At this point, the clip may be driven to move toward the distal end when the shaft is pushed to the distal end. When the clip extends out of the connecting pipe long enough, the clip may open. The clip may be driven to the proximal end when the shaft is pulled towards the proximal end. When the clip enters the channel of the connecting pipe long enough, the clip may be closed.

After the clip is closed, continuing to pull the shaft to the proximal end may drive the clip to move to the proximal end. When the clamping portion exits from the clamping hole, the connection between the clip and the shaft may be released. Edges of the clamping hole may be deformed, broken, or ruptured by the expanded portion. At this time, a separation of the connecting end and the clip may be realized, which may not affect the actual use.

Preferably, by using a suitable shape and diameter of the clamping hole, a suitable shape and width of the expanded portion, and materials surrounding the clamping hole, the expanded portion and the clamping hole may be repeatedly buckled or connected without loss.

16. A distal end of the expanded portion may include a guide portion. The cross-section of the guide portion may gradually decrease from its proximal end to its distal end. The cross-section of the guide portion may refer to a cross-section of the guide portion in a direction that is perpendicular or approximately perpendicular to the moving direction of the expanded portion towards the distal end. The cross-section of the guide portion may gradually decrease such that a guiding slope may be formed on an outer surface of the guide portion, which may guide the expanded portion to extend into the clamping hole more smoothly.

17. The clip may include at least two clip arms. The proximal end of each clip arm may include a tail clamp. There may be a space between at least two of the tail clamps, which may form the clamping hole. The clamping hole may be formed by the clip arms, thereby having a simple structure. In general, the clip arms may be flat pieces. Preferably, the proximal ends of the clip arms may be bent in a direction perpendicular or nearly perpendicular to the flat surface and form L hooks. A space between the L hooks of the two clip arms may form the clamping hole. The L hooks of the two clip arms may be symmetrically arranged with respect to the clamping hole, and the L hooks of the two clip arms may be edges of the clamping hole. In this way, the clamping hole may be formed on flat clip arms, which may have a simple structure and may be manufactured with a high production efficiency.

18. The clip may further include a connecting pin. The proximal ends of the clip arms may include a locking convex and a connecting hole. The connecting pin may be set through the connecting hole. When at least two clip arms are guided by the connecting pipe to be closed, the proximal ends of the at least two clip arms may slide along the connecting pin and bounce away from each other, and the locking convex may extend into a locking concave.

When the proximal ends of the clip arms are close to the distal end of the connecting pipe, the distal ends of the clip arms may be far apart from each other, and the clip arms may open. When the proximal ends of the clip arms are moved towards to the proximal end of the connecting pipe, the distal ends of the clip arms may be guided by the connecting pipe to be closed, the proximal ends of the clip arms may be moved away from each other, and the locking convex may extend into the locking concave, thereby the clip arms may be locked in the connecting pipe, thus preventing the clip arms from moving relative to the connecting pipe, keeping the clip arms closed, and preventing the clip from loosening after a ligation.

Preferably, the clip arms may include curvatures that allow the clip arms to automatically open or close.

Preferably, the distal end of the connecting pipe may include a blocking portion between the two clip arms. The blocking portion may block the connecting pin to prevent the clip arms from moving out of the opening of the connecting pipe at the distal end.

19. The side of the limiting convex may include a limiting portion set in the channel of the connecting pipe. When the resilient portion is extruded and expand outward, the limiting portion may abut an outer side of the limiting concave, or may abut near the limiting hole, so as to prevent the resilient portion from stretching excessively.

20. The elastic ring may be comprised of at least two half-rings that forms a connecting hole. The half-ring may include a limiting convex. The half-ring may be set directly in the channel of the connecting pipe to align the limiting convex with the limiting hole. The half-ring may be a ½ ring, a ⅓ ring, or a ring of other shapes, as long as it may automatically rebound when the connecting end exits from the connecting hole, such that the connection between the end effector device and the sheath may be released.

21. An assembly box for assembling the end effector device with the delivery device may include a body. The body may include a chamber for accommodating an end effector device and a chamber for accommodating a sheath. The chamber for accommodating the end effector device may be configured to accommodate the end effector device. The chamber for accommodating the sheath may be configured to accommodate the sheath. One end of the chamber for accommodating the sheath may be connected to the chamber for accommodating the end effector device, and the other end of the chamber for accommodating the sheath may include an opening. The end effector device may be placed in the chamber for accommodating the end effector device (including placing the entire end effector device in the chamber for accommodating the end effector device, or placing a portion of the end effector device such as the proximal end of the end effector device in the chamber for accommodating the end effector device), the distal end of the sheath may be placed in the chamber for accommodating the sheath (not limited to placing the entire sheath in the chamber for accommodating the sheath, or placing a portion of the sheath such as the distal end of the sheath in the chamber for accommodating the sheath), and the sheath may be pushed from the opening of the chamber for accommodating the sheath such that the sheath may be placed outside the resilient portion, or the connecting pipe may be placed outside the resilient portion. The chamber for accommodating the sheath may guide the sheath to connect with the proximal end of the end effector device, thus facilitating the connection between the sheath and the end effector device.

22. The chamber for accommodating the end effector device may include a chamber for accommodating a clip and a chamber for accommodating a connecting pipe connected to the chamber for accommodating the clip. The chamber for accommodating the clip may be configured to accommodate the clip, and the chamber for accommodating the connecting pipe may be configured to accommodate the connecting pipe.

23. A positioning convex may be located between the chamber for accommodating the clip and the chamber for accommodating the connecting pipe. The positioning convex may be configured to abut a distal end of the connecting pipe, so as to prevent the connecting pipe from sliding to the chamber for accommodating the clip, provide support for the connecting pipe, and avoid a movement of the connecting pipe when connecting and/or separating the end effector device and the sheath by moving the connection end.

24. The chamber for accommodating the clip may accommodate the clip in an open state. The clamping hole of the clip may be set at a front end of the connecting hole. After the connecting end passes through the connecting hole, the clamping portion may be connected to the clamping hole, thus the clip may be in an open state in advance. At this point, the clamping hole may be close to the distal end of the connecting pipe. First, the connecting end may be inserted into the connecting hole of the resilient portion, such that the end effector device may be connected with the sheath, the connecting end may continue to move towards the distal end, and the clamping portion may be connected with the clamping hole. At this point, the shaft may be connected with the clip. When the shaft is pulled to move towards the proximal end, the clip may be pulled into the connecting pipe, then the delivery device and the end effector device may be pulled out together from the opening of the chamber for accommodating the sheath. At this point, a connection between the end effector device and the delivery device may be accomplished, and a connection between the shaft and the clip may also be accomplished. The clip may be operated for ligation by operating the shaft, thus the assembly of the end effector device and the delivery device may be completed.

25. The body may include an accommodate section and a clamping section connected to each other. The accommodate section may include the chamber for accommodating the end effector device. The clamping section may include the chamber for accommodating the sheath. The chamber for accommodating the sheath may be deformed for clamping the sheath when the clamping section is subjected to an extrusion force. When in use, the clamping section may be clamped by hand to stabilize the sheath, such that the sheath and the connecting pipe may be always in a docking position, which may facilitate the connection of the sheath and the connecting pipe.

26. The clamping section may include at least two clamping pieces. At least two of the clamping pieces may form the chamber for accommodating the sheath. When the clamping pieces are subjected to an extrusion force, at least two of the clamping pieces may be moved towards each other for clamping the sheath. The clamping section may utilize the clamping pieces to achieve the clamping function. When the clamping pieces open, the sheath may be inserted into the chamber for accommodating the sheath, and then an extrusion force may be applied to the clamping pieces to clamp the sheath.

DESCRIPTION OF REFERENCE SIGNS

100, end effector device, 110, clamping arm, 111, locking convex, 112, tail clamp, 113, ligation tooth, 114, coupling hole, 115, clamping hole, 120, connecting pipe, 121, limiting hole, 122, locking concave, 123, blocking portion, 130, connecting pin, 140, positioning groove, 150, positioning ring;

200, delivery device, 210, sheath, 220, shaft, 230, connecting end, 231, expanded portion, 232, recessed portion, 233, guide portion, 240, limiting concave, 250, end cover, 270, limiting step;

300, control device, 310, handle, 320, sliding portion;

400, elastic ring, 410, limiting convex, 420, limiting portion, 430, connecting hole, 440, notch, 450, resilient portion, 460, half-ring;

500, assembly box, 510, accommodate section, 511, chamber for accommodating a clip, 512, chamber for accommodating a connecting pipe, 513, positioning convex, 520, clamping section, 521, chamber for accommodating a sheath, 522, clamping piece.

DETAILED DESCRIPTION

The present disclosure will be further described in detail below, but the implementation of the present disclosure is not limited thereto.

Embodiment One

Figure 1:
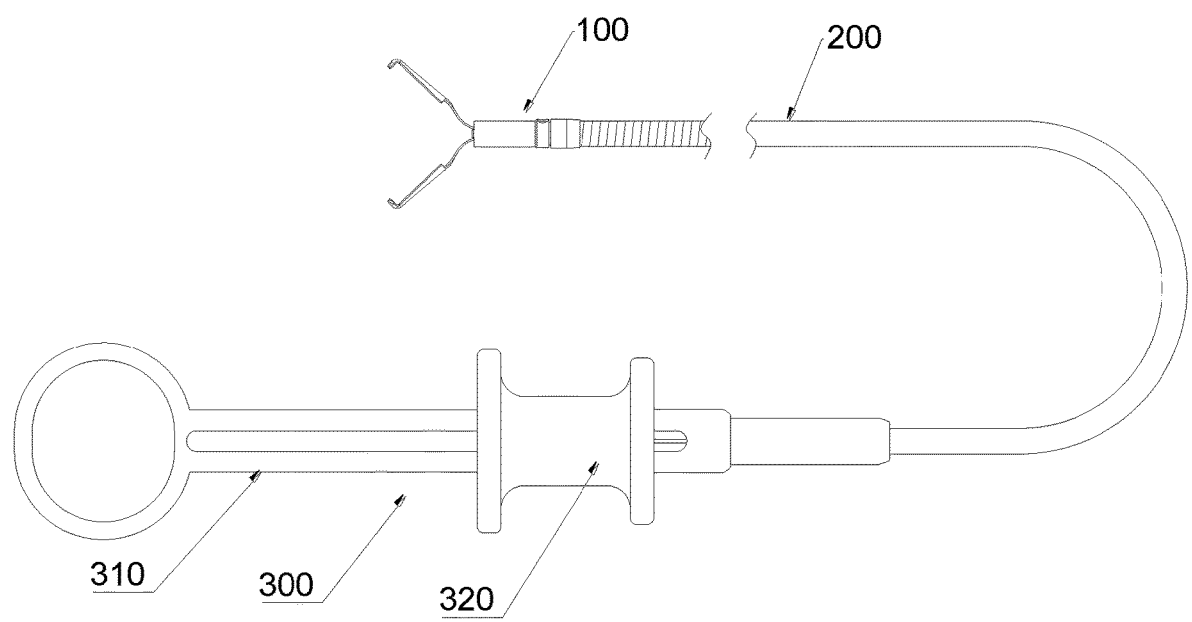
FIG. 1 is a schematic diagram illustrating an overall structure of an end effector instrument according to embodiment one of the present disclosure.
Figure 2:
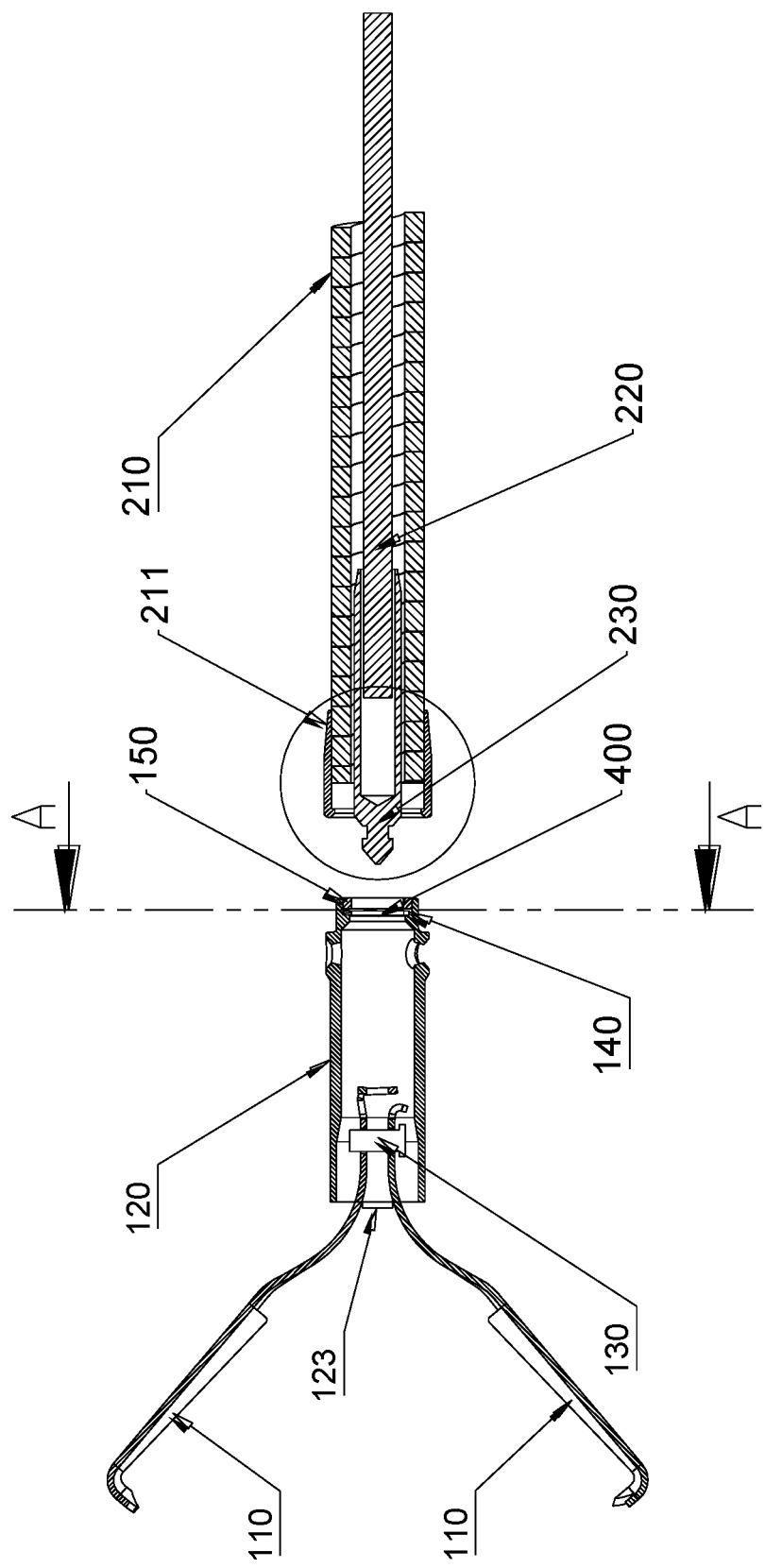
FIG. 2 is a schematic diagram illustrating an end effector device and a delivery device in an unconnected state according to embodiment one of the present disclosure.
Figure 3:
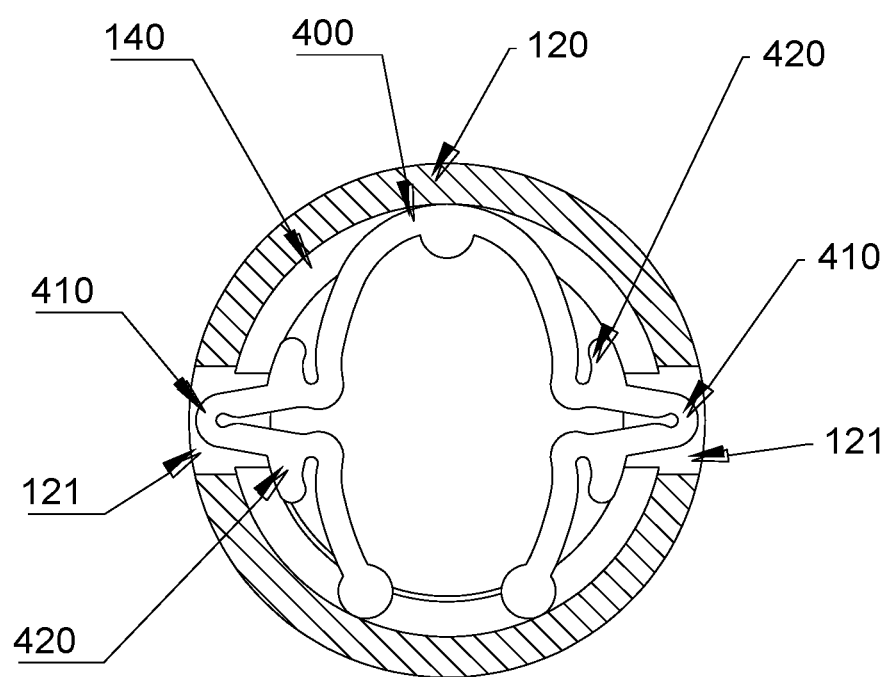
FIG. 3 is a schematic diagram illustrating an A-A cross-sectional view of FIG. 2.

As shown in FIG. 1, an end effector instrument may include an end effector device 100, a delivery device 200, and a control device 300.

As shown in FIGS. 2 to 16, the end effector device 100 may include a clip, a connecting pipe 120, and an elastic ring 400. The clip may be mounted on the connecting pipe 120, and the connecting pipe 120 may include a channel. A proximal end of the clip may extend into or exit from the channel of the connecting pipe 120 through a distal end of connecting pipe 120. The clip may include two clip arms 110 connected at the proximal ends. The distal ends of the clip arms 110 may include ligation teeth 113. A distal end of the connecting pipe 120 may include a blocking portion 123 between the two clip arms 110 for blocking the clip arms 110 or the connecting pin 130, so as to prevent the clip arms 110 from moving out of the distal end of the connecting pipe 120. When the distal ends of the clip arms 110 are close to the distal end of the connecting pipe 120, the clip arms 110 may be constrained by the connecting pipe 120 to be closed.

The resilient portion may include an elastic ring 400. The elastic ring 400 may include a connecting hole 430. An outer peripheral surface of the elastic ring 400 may include a limiting convex 410. The elastic ring 400 may be set in the channel of the connecting pipe 120. The elastic ring 400 may include the connecting hole 430 and the limiting convex 410. The connecting hole 430 may be connected to the channel of the connecting pipe 120. A pipe wall of the connecting pipe 120 may include a limiting hole 121 corresponding to the limiting convex 410. The limiting convex 410 may pass through or exit from the limiting hole 121.

The delivery device 200 may include a sheath 210 and a shaft 220. The sheath 210 may include a passage. The shaft 220 may be accommodated in the passage of the sheath 210. A distal end of the shaft 220 may include a connecting end 230. The sheath 210 may include a sheath body and an end cover 250. The end cover 250 may include a limiting step 270, which may form a limiting concave 240 with a surface of the distal end of the sheath body.

The control device 300 may include a handle 310 and a sliding portion 320. The handle 310 may be connected to the sheath 210. The sliding portion 320 may be connected to the shaft 220. The sliding portion 320 may slide relative to the handle 310 towards a distal end or a proximal end, to cause the shaft 220 to move relative to the sheath 210 towards the distal end or the proximal end.

When the sheath 210 is placed outside the elastic ring 400, the connecting end 230 may extend into or exit from the connecting hole 430. When the connecting end 230 extends into the connecting hole 430, the elastic ring 400 may expand laterally outward, the limiting convex 410 may extend into the limiting concave 240 to connect the connecting pipe 120 with the sheath 210. When the connecting end 230 exits from the connecting hole 430, the elastic ring 400 may rebound, and the limiting convex 410 may exit from the limiting concave 240 to release the connection between the connecting pipe 120 and the sheath 210.

Figure 10:
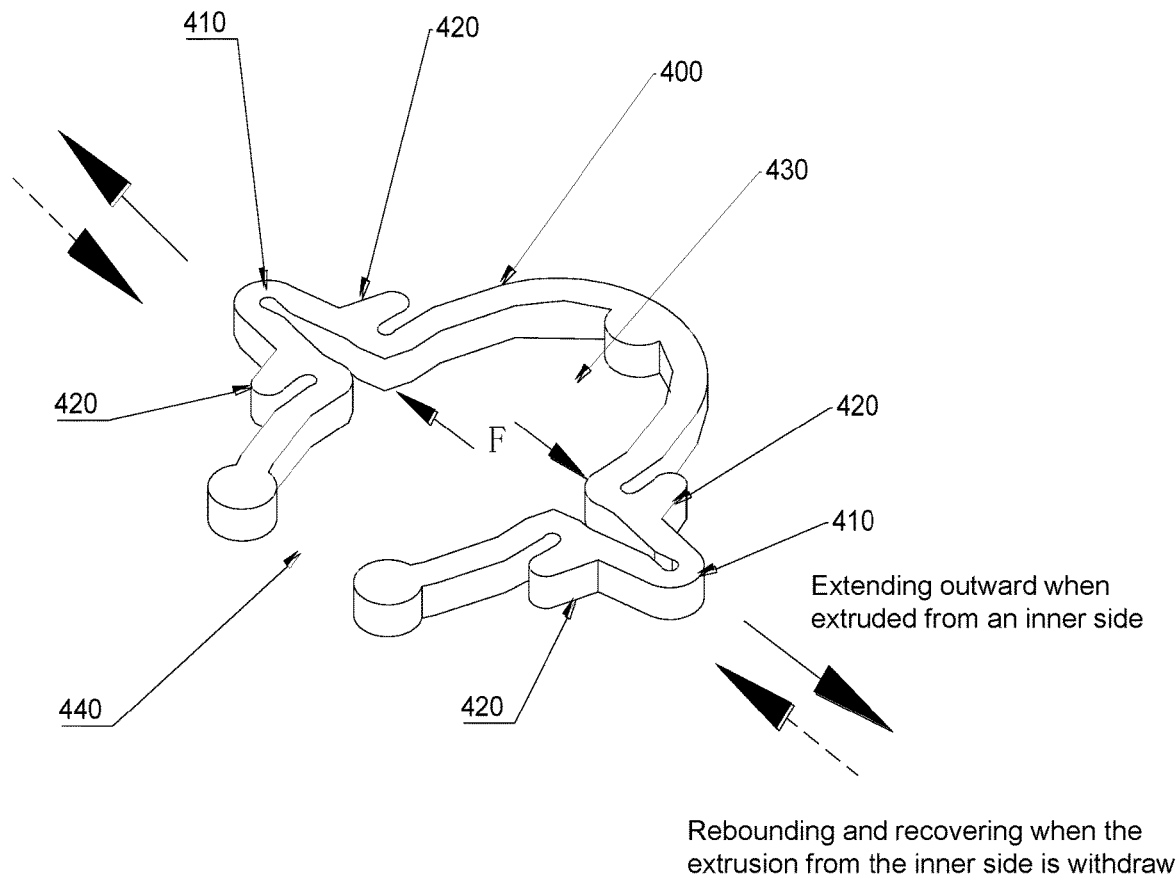
FIG. 10 is a schematic diagram illustrating an elastic ring according to embodiment one of the present disclosure.
Figure 11:
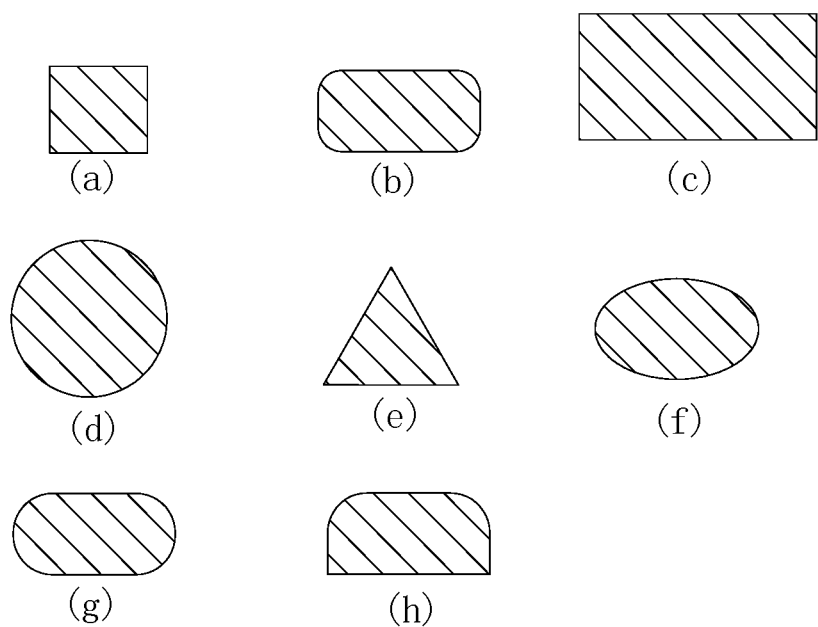
FIG. 11 is a schematic diagram illustrating a cross-section of the elastic ring according to embodiment one of the present disclosure.

When the elastic ring 400 is subjected to an extrusion force (in the direction along force F illustrated in FIG. 10) applied from the connecting hole 430, the elastic ring 400 may expand outward (in the pointing direction of the solid arrow illustrated in FIG. 10). When the extrusion force applied from the connecting hole 430 on the elastic ring 400 is withdrawn, the elastic ring 400 may rebound (in the pointing direction of the dashed arrow illustrated in FIG. 10). The elastic ring 400 may include a notch 440. The notch 440 may increase the degree of an expansion of the elastic ring 400 as it is extruded, such that the connection between the limiting convex 410 and the limiting concave 240 may be stable. At the same time, it may also cause the connecting end 230 to be inserted into the connecting hole 430 more easily. The shape of the cross-section of the elastic ring 400 may not be limited. Preferably, shapes of (a) to (h) as shown in FIG. 11 may be used.

In some embodiments, the limiting concave 240 may be a groove on an inner wall of the sheath 210. The sheath 210 may include the sheath body and the end 250 set at the distal end of the sheath body. The end cover 250 may include the limiting step 270. The end cover 250 may be set to form the limiting concave 240. The production process may be simple, but not be limited thereto. A blind hole, a through hole, or a groove on a side wall of the sheath 210 may be generated to form the limiting concave 240. Or a step protruding towards a central axis of the sheath 210 on the inner wall of the sheath 210 may also be provided. The limiting concave 240 may be formed between the step and the inner wall of the sheath 210, for limiting the limiting convex 410 from sliding out of the distal end of the sheath 210.

Figure 9:
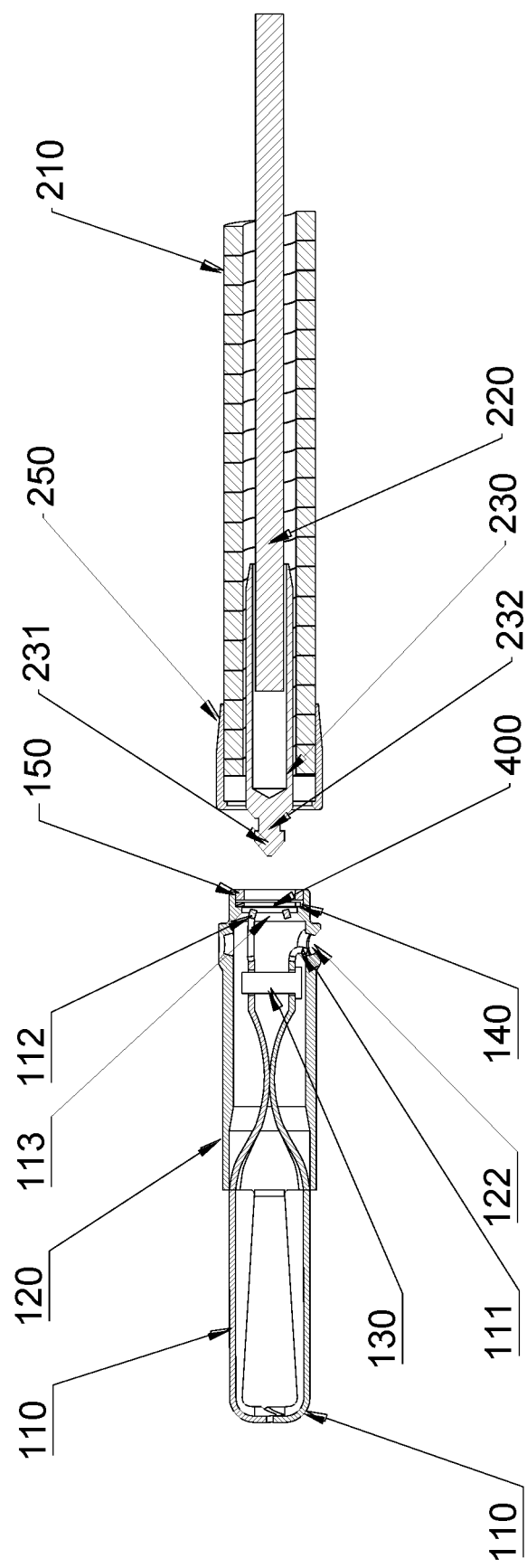
FIG. 9 is a schematic diagram illustrating an end effector device and a delivery device released from the end effector after the clip is closed according to embodiment one of the present disclosure.
Figure 12:
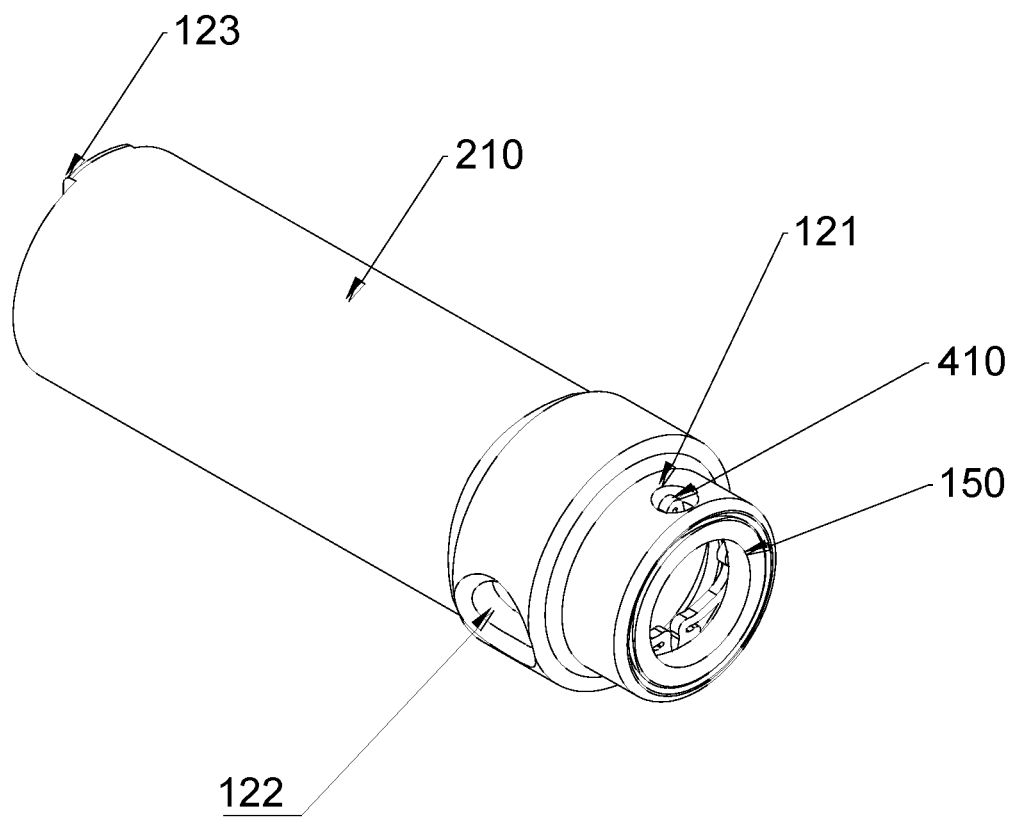
FIG. 12 is a schematic diagram illustrating a connecting pipe and an elastic ring according to embodiment one of the present disclosure.
Figure 13:
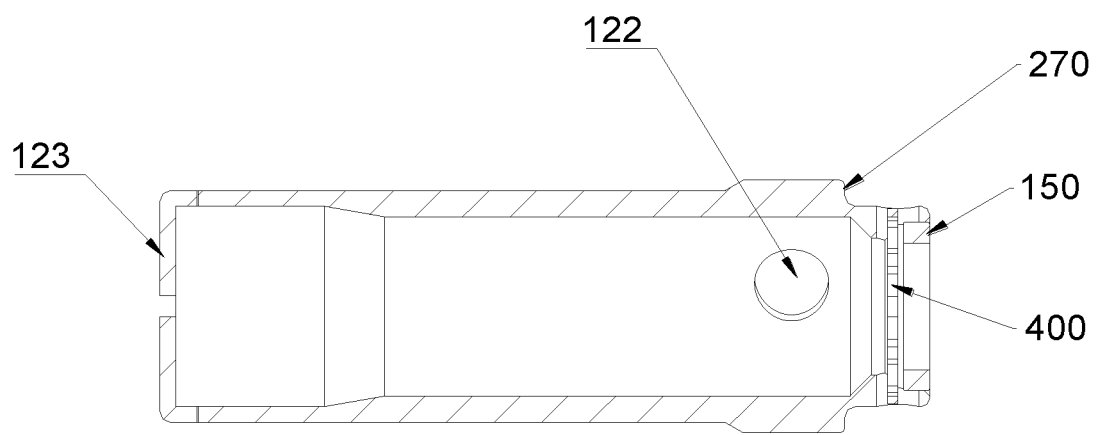
FIG. 13 is a schematic diagram illustrating a cross-sectional view of the connecting pipe and the elastic ring according to embodiment one of the present disclosure.

In some embodiments, as shown in FIG. 9, FIG. 10 and FIG. 12, a proximal end of the connecting pipe 120 may include a positioning ring 150. An inner wall of the connecting pipe 120 may include a step. The elastic ring 400 may be mounted on the proximal end of the connecting pipe 120 by the step and the positioning ring 150. However, it is not limited thereto, the elastic ring 400 may be set in the channel of the connecting pipe 120 directly, such that the limiting convex 410 of the elastic ring 400 may extend into the limiting hole 121. Or any other positioning structure by which the elastic ring 400 is mounted may also be set in the connecting pipe 120.

A side of the limiting convex 410 may include a limiting portion 420. The limiting portion 420 may be set in the channel of the connecting pipe 120. When the elastic ring 400 is extruded and expands outward, the limiting portion 420 may abut an outer side of the limiting concave 240, or may abut the limiting hole 121, so as to prevent the elastic ring 400 from stretching excessively.

Figure 16:
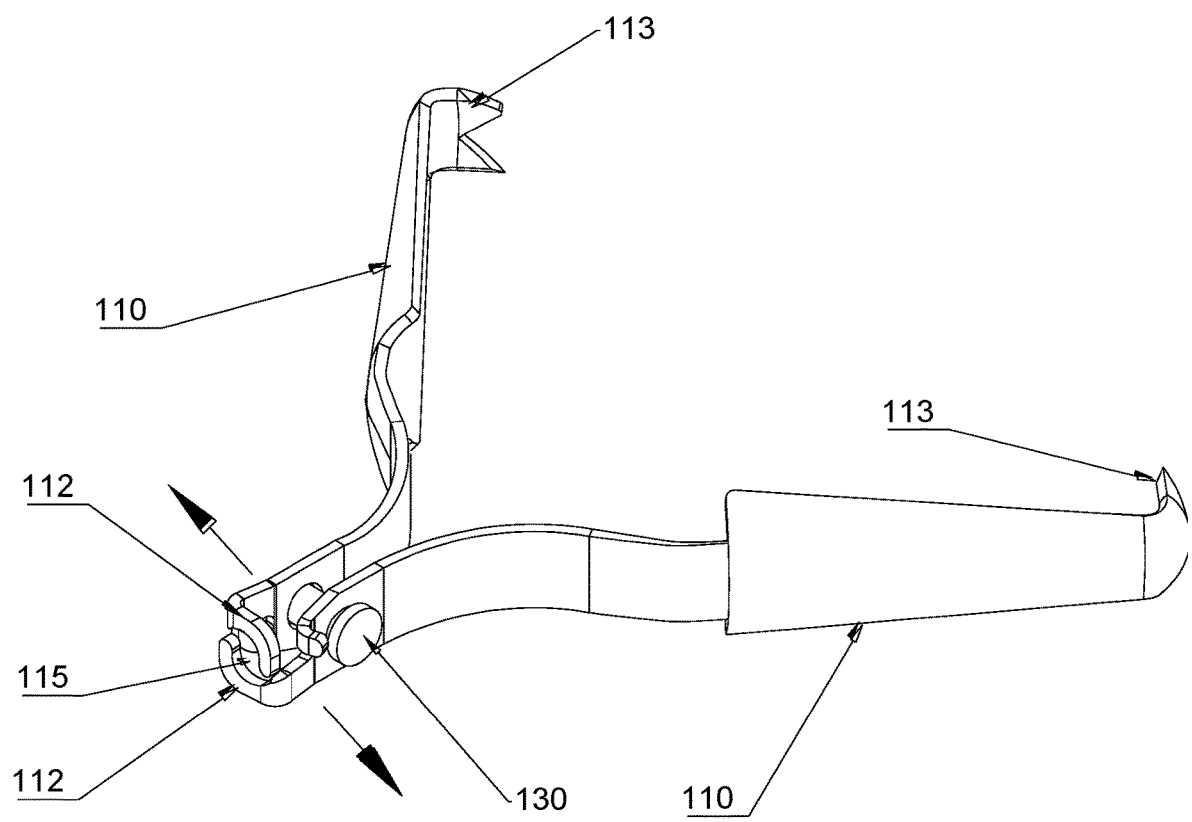
FIG. 16 is a schematic diagram illustrating a clip according to embodiment one of the present disclosure.

The proximal end of each clip arm 110 may include a tail clamp 112. There may be a space between two tail clamps 112, which may form a clamping hole 115. The clamping hole 115 may be connected to the channel of the connecting pipe 120. The clamping hole 115 may be formed by the clip arms 110 directly, thereby having a simple structure. In general, the clip arms 110 may be flat pieces. Preferably, the proximal ends of the clip arms 110 may be bent in a direction perpendicular or nearly perpendicular to the flat surface and form L hooks. As shown in FIG. 16, the space between the L hooks of the two clip arms 110 may form the clamping hole 115. The L hooks of the two clip arms 110 may be symmetrically arranged with respect to the clamping hole 115, and the L hooks of the two clip arms 110 may be the edges of the clamping hole 115. In this way, the clamping hole 115 may be formed on the clip arms 110, which may have a simple structure and may be manufactured with a high production efficiency.

A distal end of the connecting end 230 may include a clamping portion matched with the clamping hole 115. The clamping portion may include a recessed portion 232 and an expanded portion 231. The recessed portion 232 may be located between the expanded portion 231 and the connecting end 230. The maximum width (D1 as illustrated in FIG. 14) of the expanded portion 231 may be greater than the minimum width (D2 as illustrated in FIG. 14) of the recessed portion 232, and greater than the minimum width of the clamping hole 115.

The clip may further include a connecting pin 130. The proximal ends of the clip arms 110 may include a locking convex 111 and a coupling hole 114. The connecting pin 130 may be set through the coupling hole 114. When the two clip arms 110 are constrained by the connecting pipe 120 to be closed, the proximal ends of the two clip arms 110 may slide along the connecting pin 130 and move away from each other (in the pointing direction of the arrows illustrated in FIG. 16), and the locking convex 111 may extend into a locking concave 122.

When the proximal ends of the clip arms 110 are close to the distal end of the connecting pipe 120, the distal ends of the clip arms 110 may be far apart from each other, and the clip arms 110 may open. When the proximal ends of the clip arms 110 are close to the proximal end of the connecting pipe 120, the distal ends of the clip arms 110 may be constrained by the connecting pipe 120 to be closed, the proximal ends of the clip arms 110 may move away from each other, and the locking convex 111 may extend into the locking concave 122, thereby the clip arms 110 may be locked in the connecting pipe 120, thus preventing the clip arms 110 from moving relative to the connecting pipe 120, keeping the clip arms 110 closed, and preventing the clip from loosening after ligation. Preferably, the clip arms 110 may include curvatures that allow the clip arms 110 to automatically open or close.

Figure 4:
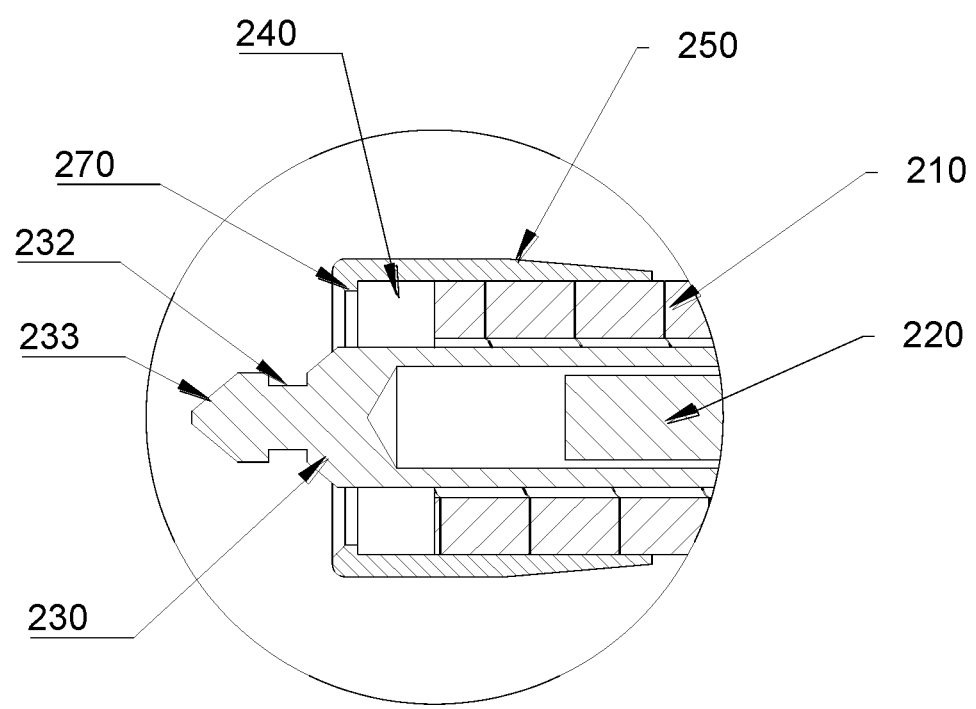
FIG. 4 is a schematic diagram illustrating an enlarged view of the circled part of FIG. 2.
Figure 5:
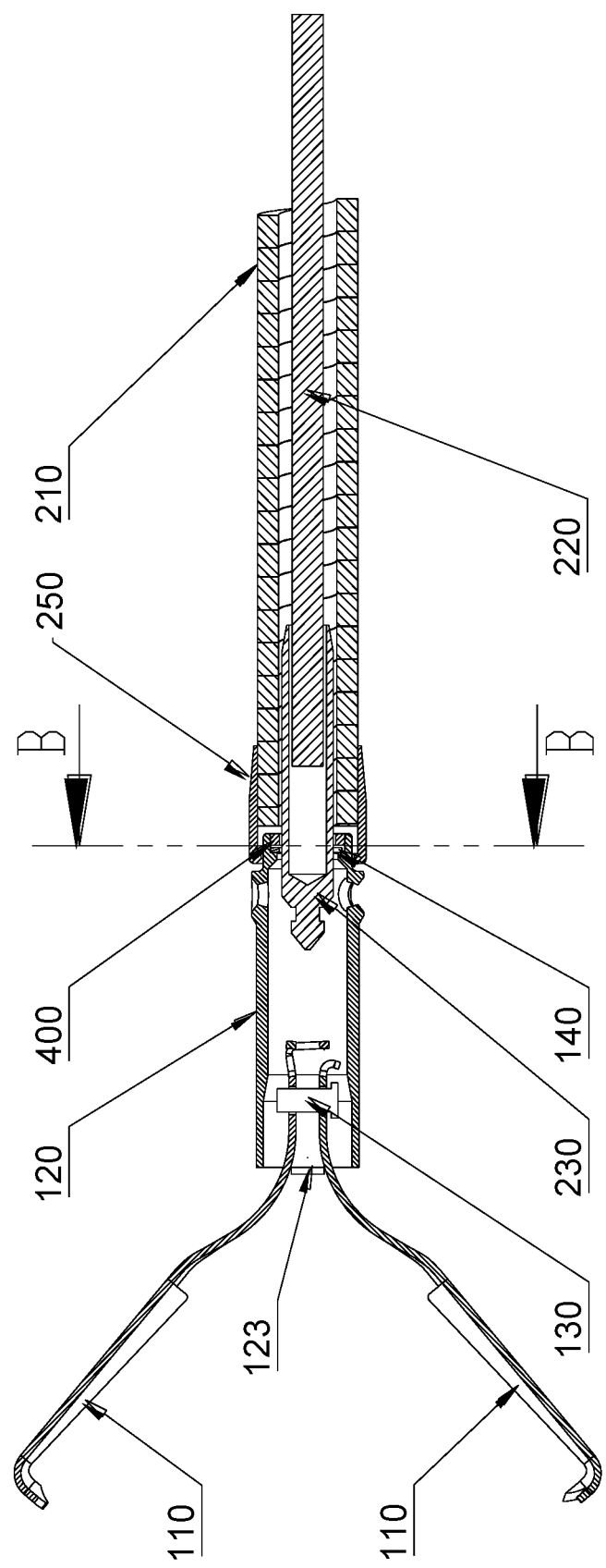
FIG. 5 is a schematic diagram illustrating an end effector device and a delivery device in a connected state according to embodiment one of the present disclosure.
Figure 6:
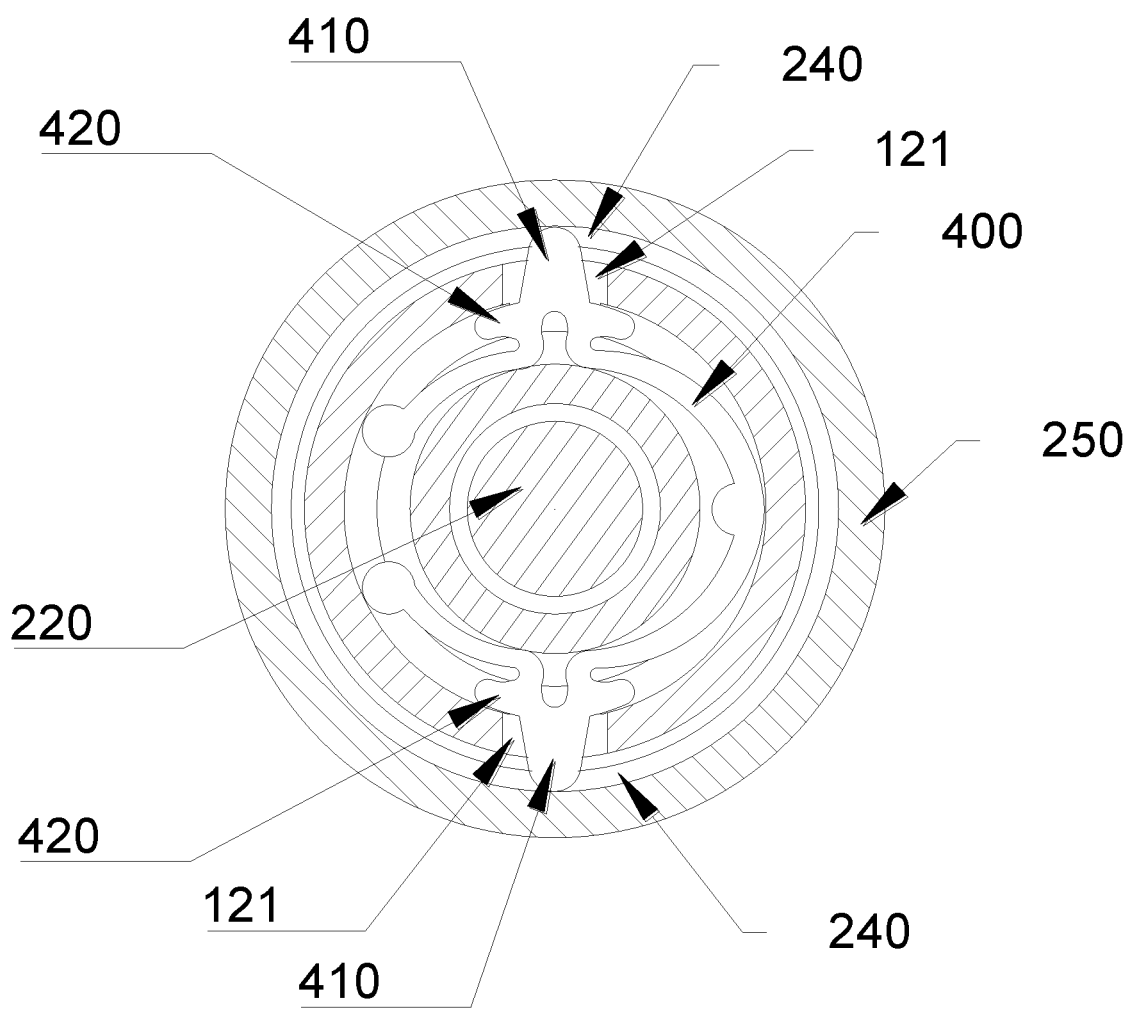
FIG. 6 is a schematic diagram illustrating a B-B cross-sectional view of FIG. 5.
Figure 7:
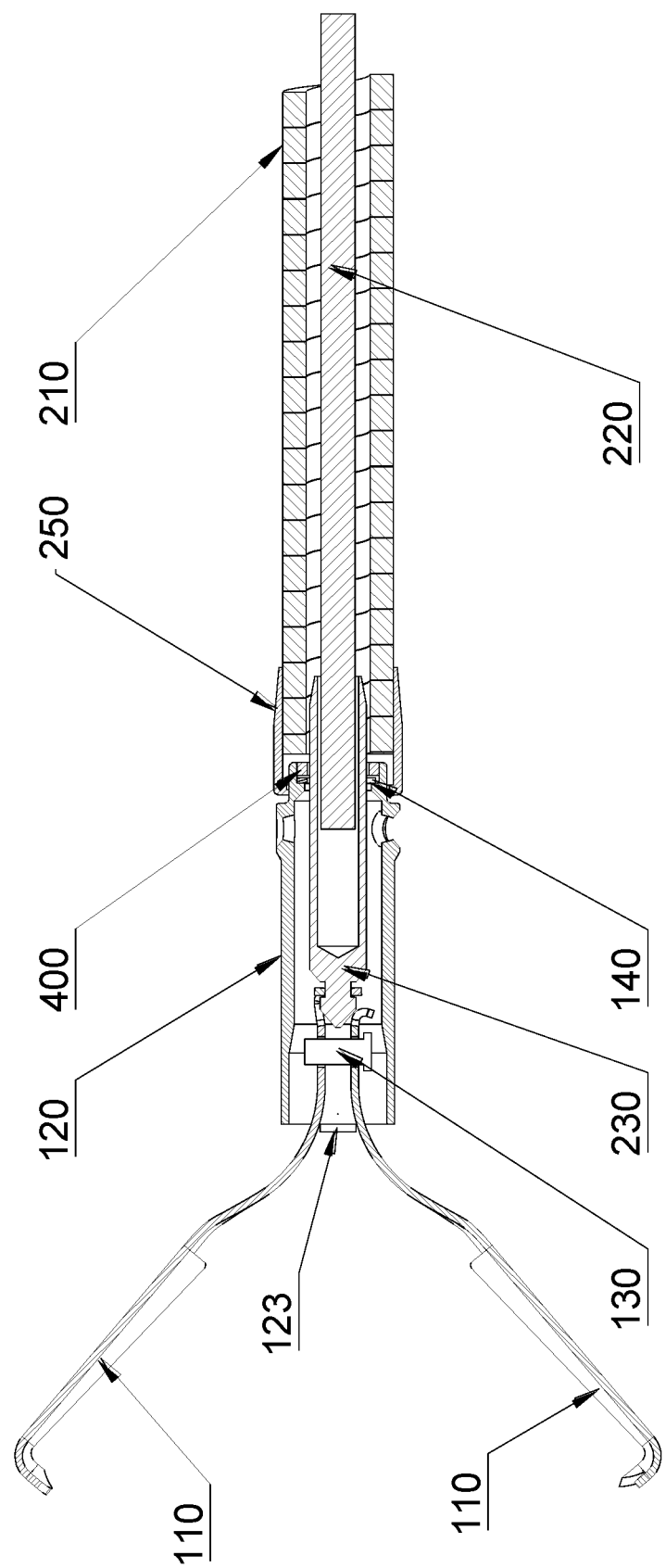
FIG. 7 is a schematic diagram illustrating a connecting end and a clip in a connected state according to embodiment one of the present disclosure.
Figure 8:
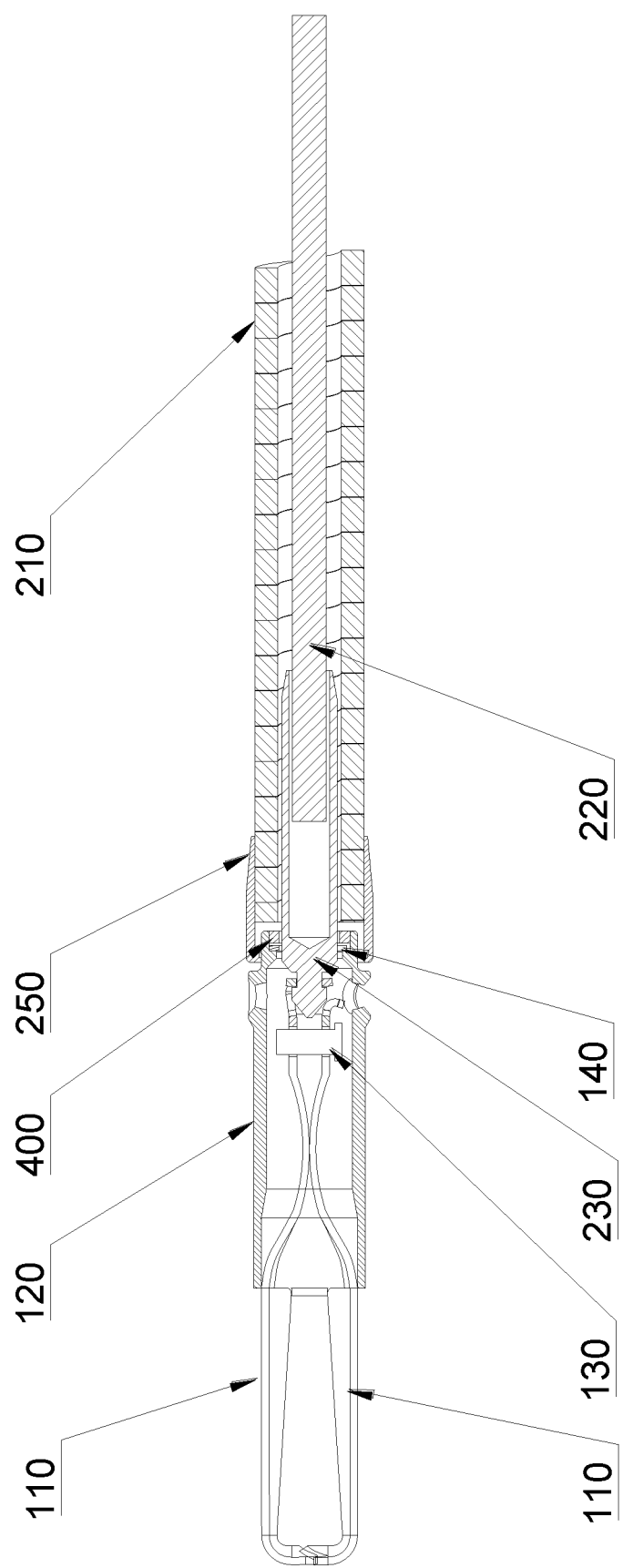
FIG. 8 is a schematic diagram illustrating a clip in a closed state according to embodiment one of the present disclosure.
Figure 14:
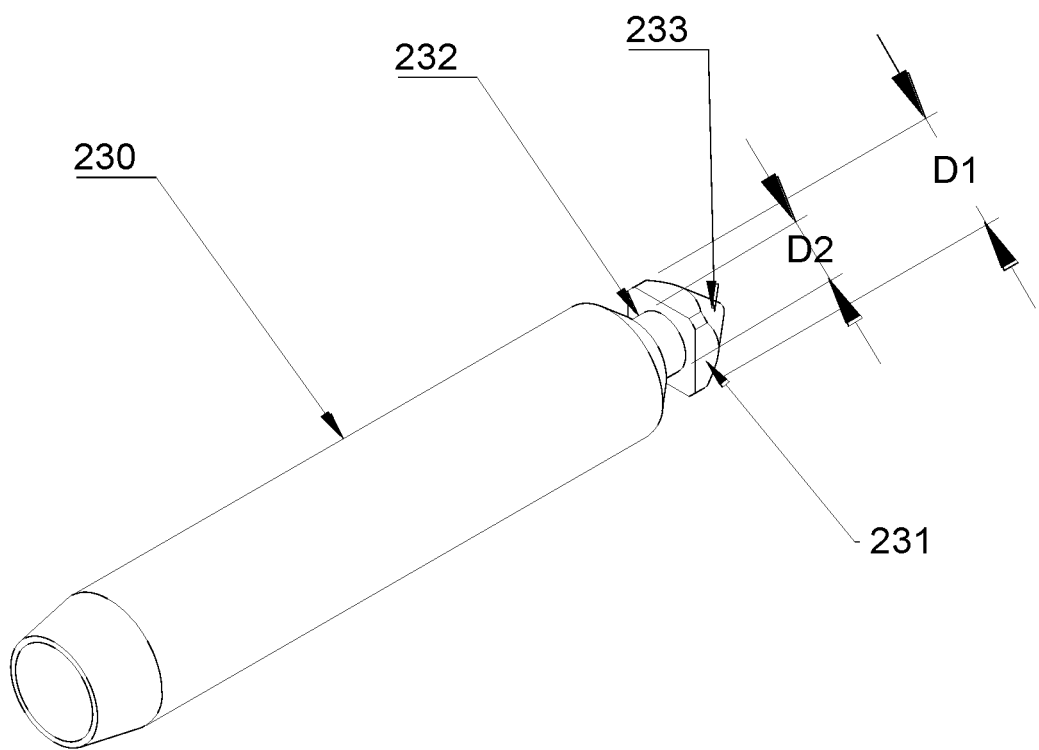
FIG. 14 is a schematic diagram illustrating a connecting end according to embodiment one of the present disclosure.
Figure 15:
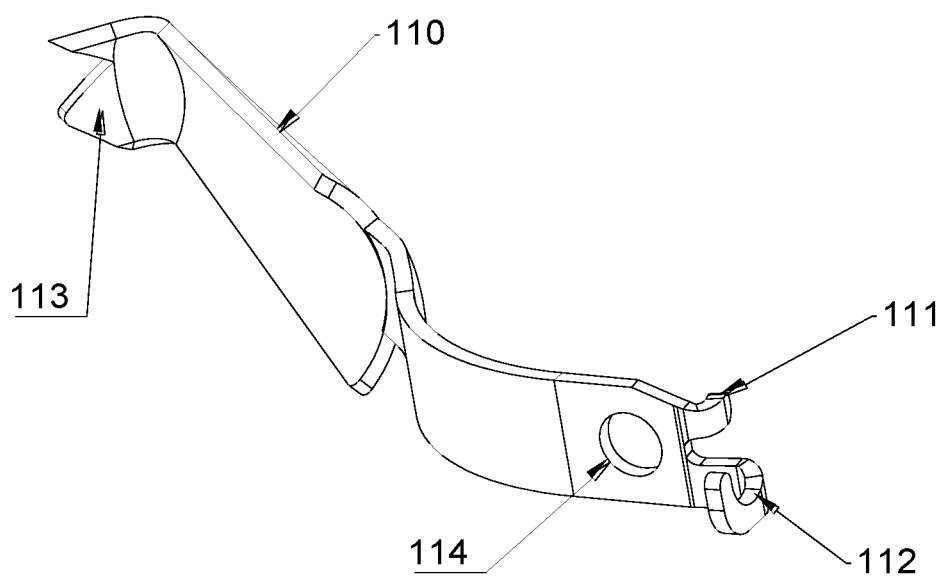
FIG. 15 is a schematic diagram illustrating a clamping arm according to embodiment one of the present disclosure.

As shown in FIG. 4 and FIG. 14, a distal end of the expanded portion 231 may include a guide portion 233. The cross-section of the guide portion 233 may gradually decrease from its proximal end to its distal end. The cross-section of the guide portion 233 may refer to a cross-section of the guide portion 233 in a direction that is perpendicular or approximately perpendicular to the moving direction of the expanded portion 231 towards the distal end. The cross-section of the guide portion 233 may gradually decrease such that a guiding slope may be formed on an outer surface of the guide portion 233, which may guide the expanded portion 231 to extend into the clamping hole 115 more smoothly.

After the clip is closed, continuing to pull the shaft 220 to the proximal end may drive the clip to move to the proximal end. When the clamping portion exits from the clamping hole 115, the connection between the clip and the shaft 220 may be released. Edges of the clamping hole 115 may be deformed, broken, or ruptured by the expanded portion 231. At this time, a separation of the connecting end 230 and the clip may be realized, which may not affect the actual use.

Preferably, by using a suitable shape and diameter of the clamping hole 115, a suitable shape and width of the expanded portion 231, and materials surrounding the clamping hole 115, the expanded portion 231 and the clamping hole 115 may be repeatedly buckled or connected without loss.

In some embodiments, the end effector device 100 and the delivery device 200 may be repeatedly connected and disconnected. After the end effector device 100 ligates a human body, the end effector device 100 may be detached from the delivery device 200, and the delivery device 200 may be recycled. The end effector device 100 and the delivery device 200 may be separately produced, and then assembled for use. FIG. 17 to FIG. 23 illustrate a method for assembling the end effector device 100 and the delivery device 200. In some embodiments, an assembly box 500 may be used for assembly, with a high success rate and simple operation, which may improve assembly efficiency and facilitate the use for a medical staff after a quick training.

Figure 17:
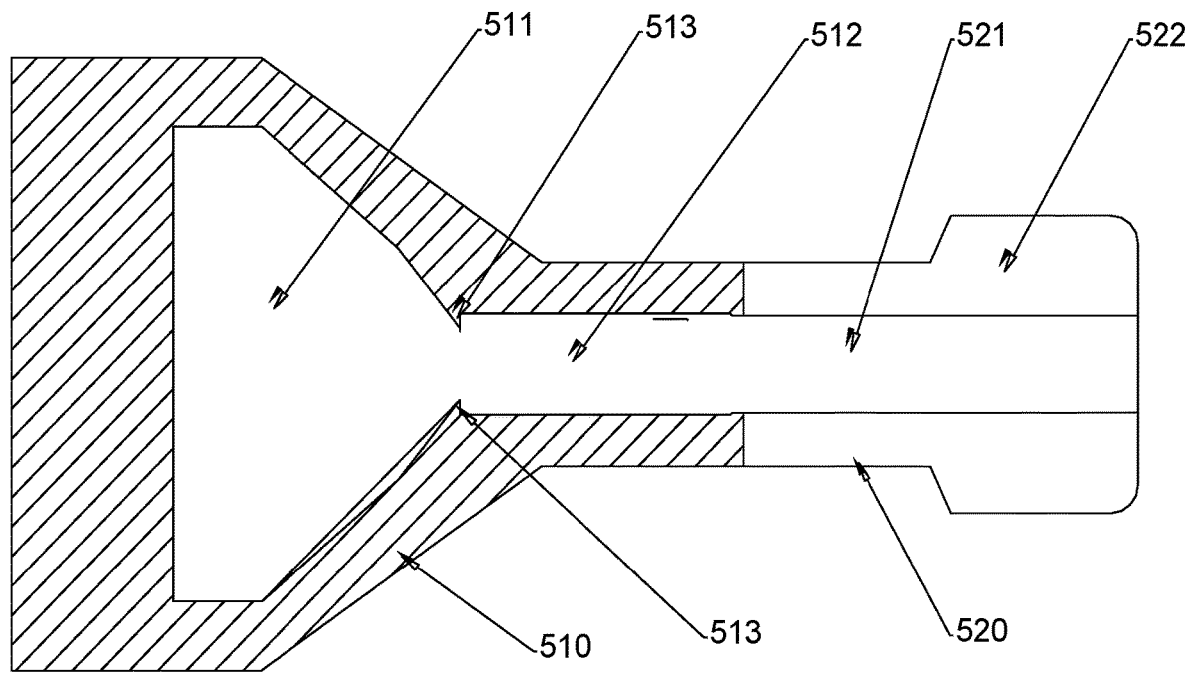
FIG. 17 is a schematic diagram illustrating an assembly box according to embodiment one of the present disclosure.

As shown in FIG. 17, the assembly box 500 may include a body. The body may include an accommodate section 510 and a clamping section 520 connected to each other. The accommodate section 510 may include a chamber for accommodating the end effector device 100 including a chamber 511 for accommodating the clip and a chamber for accommodating the connecting pipe 120 connected to the chamber 511 for accommodating the clip. The chamber 511 for accommodating the clip may be configured to accommodate the clip, and the chamber for accommodating the connecting pipe may be configured to accommodate the connecting pipe 120.

The chamber 511 for accommodating the clip may accommodate the clip in an open state.

A positioning convex 513 may be provided between the chamber 511 for accommodating the clip and the chamber for accommodating the connecting pipe 120. The positioning convex 513 may abut a distal end of the connecting pipe 120.

The clamping section 520 may include a chamber for accommodating the sheath 210. One end of the chamber for accommodating the sheath 210 may be connected to the chamber for accommodating the end effector device 100, and another end of the chamber for accommodating the sheath 210 may include an opening.

When the clamping section 520 is subjected to an extrusion force (in the pointing direction of the arrows illustrated in FIG. 19), the minimum width of the chamber for accommodating the sheath 210 may be reduced.

Figure 19:
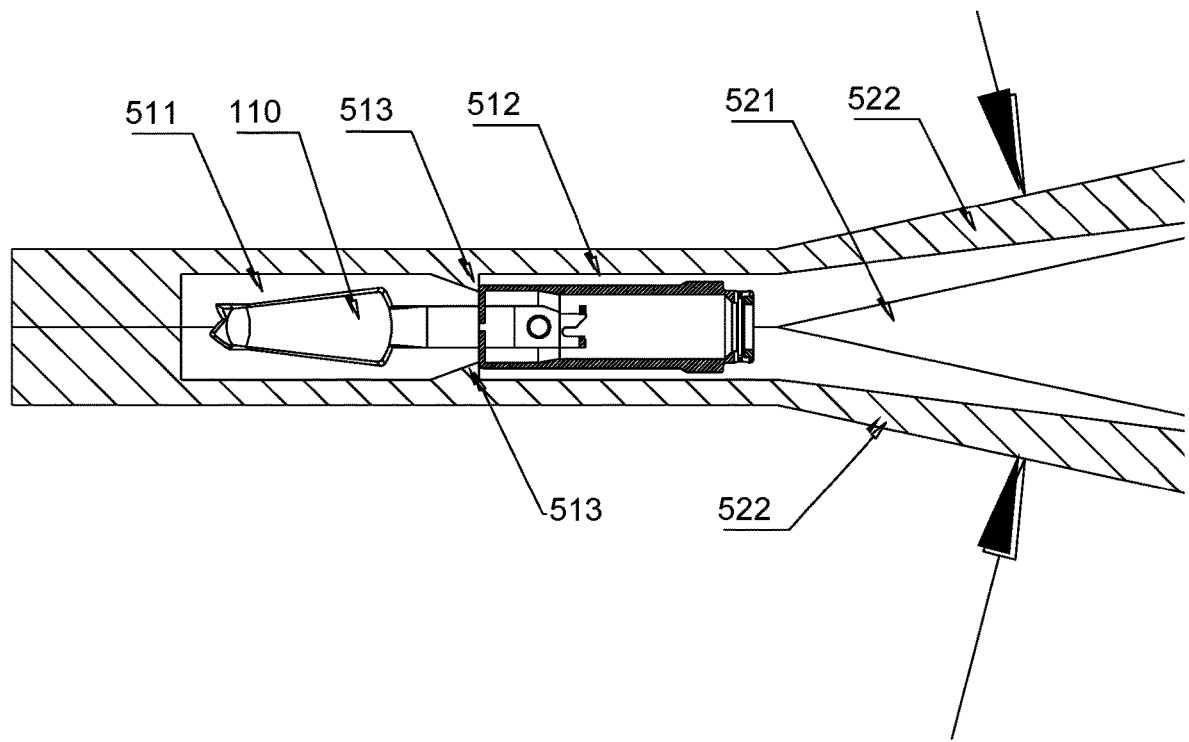
FIG. 19 is a schematic diagram illustrating a top view of FIG. 18.

As shown in FIG. 19, the clamping section 520 may include at least two clamping pieces 522. The at least two clamping pieces 522 may form the chamber for accommodating the sheath 210. When the clamping pieces 522 are subjected to an extrusion force, the at least two clamping pieces 522 may be moved towards each other, and the minimum width of the chamber for accommodating the sheath 210 may be reduced.

Figure 18:
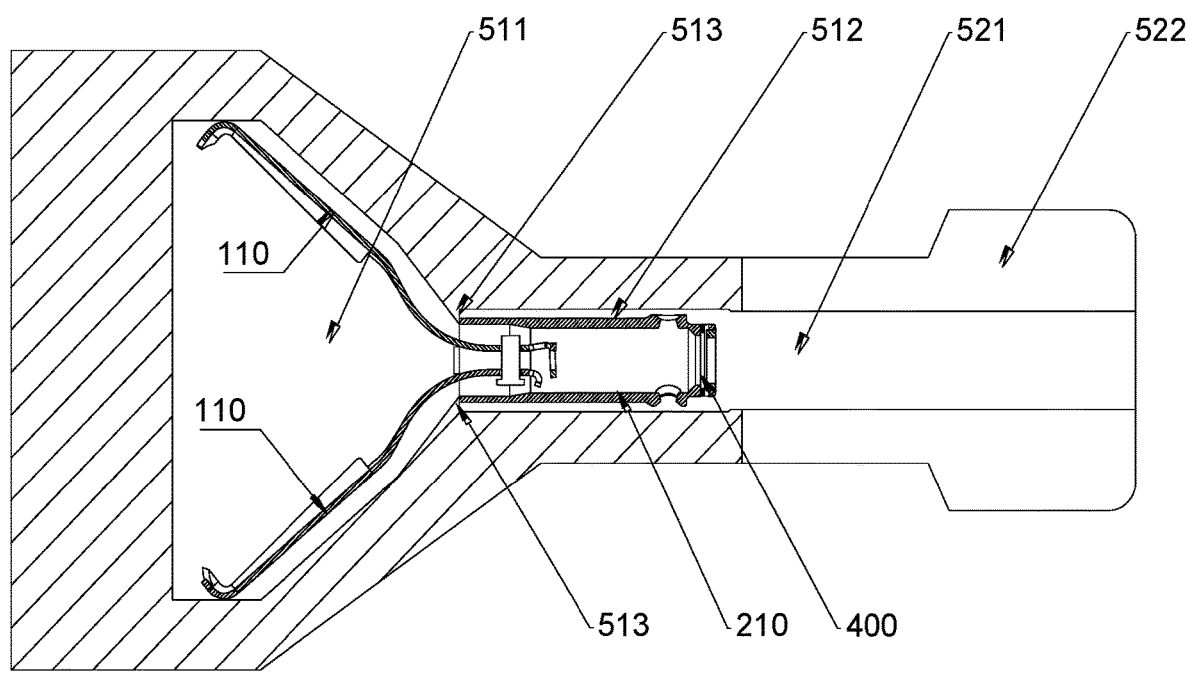
FIG. 18 is a schematic diagram 1 illustrating the assembly method according to embodiment one of the present disclosure.

In an assembly:

(1) As shown in FIG. 18 and FIG. 19, the end effector device 100 may be placed in the chamber for accommodating the end effector device 100. The clip in an open state may be accommodated in the chamber 511 for accommodating the clip. The connecting pipe 120 may be accommodated in the chamber for accommodating the connecting pipe 120, and the distal end of connecting pipe 120 may abut the positioning convex 513.

Figure 20:
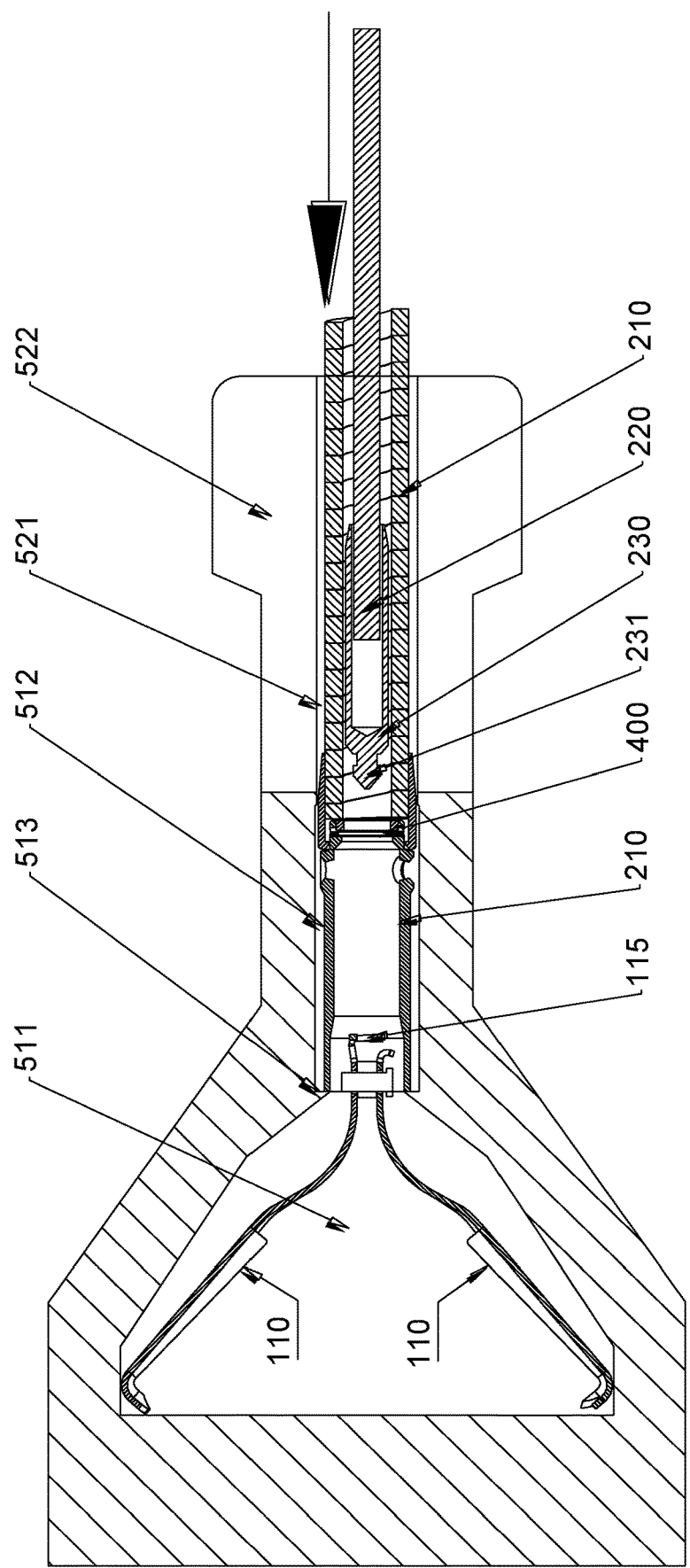
FIG. 20 is a schematic diagram 2 illustrating an assembly method according to embodiment one of the present disclosure.

(2) The sheath 210 may be inserted from the opening at the proximal end of the chamber for accommodating the sheath 210 such that the sheath 210 may be placed outside the proximal end of the connecting pipe 120. At this time, as shown in FIG. 20, the sheath 210 may be set outside the elastic ring 400. The clamping pieces 522 of the clamping portion may be extruded (as indicated by the arrow in FIG. 20) such that the clamping pieces 522 may fix the position of the sheath 210 for further operations.

Figure 21:
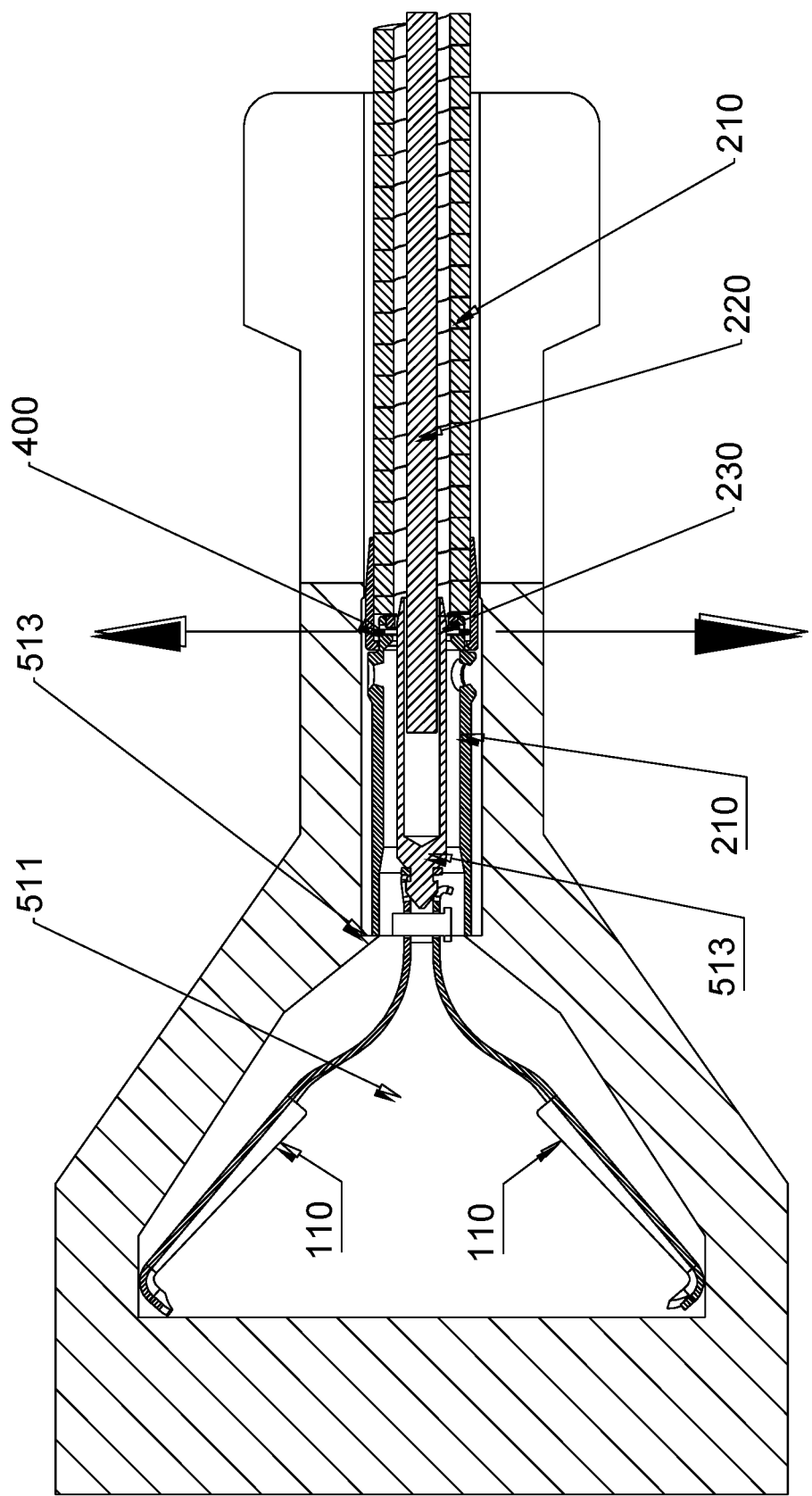
FIG. 21 is a schematic diagram 3 illustrating an assembly method according to embodiment one of the present disclosure.
Figure 22:
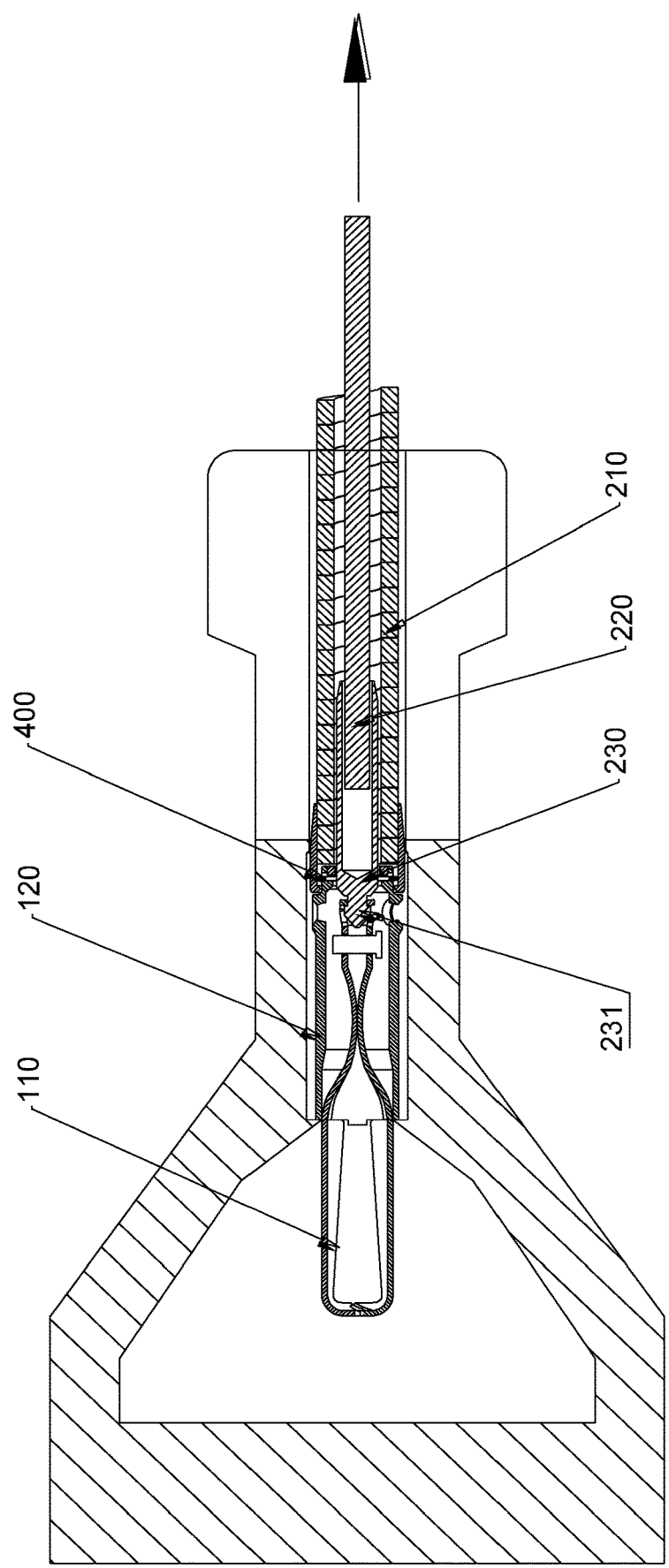
FIG. 22 is a schematic diagram 4 illustrating an assembly method according to embodiment one of the present disclosure.
Figure 23:
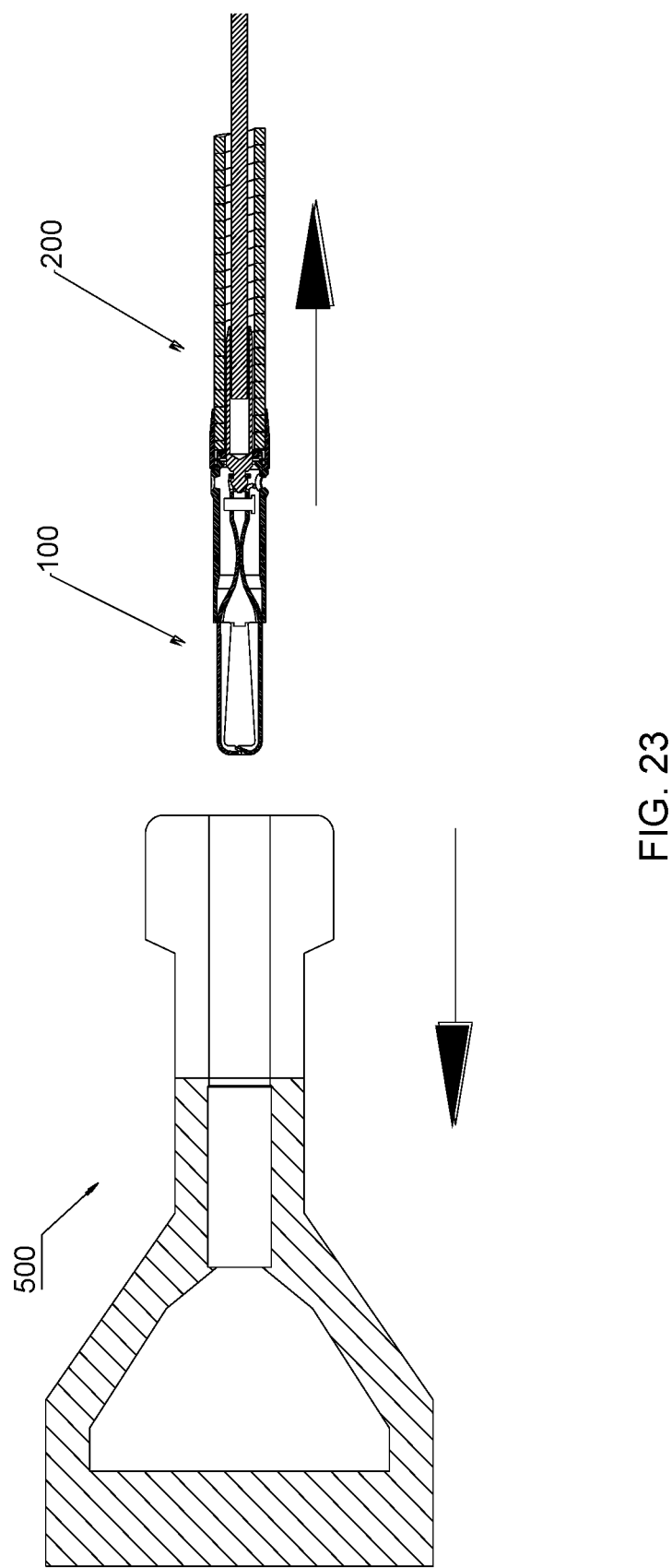
FIG. 23 is a schematic diagram 5 illustrating an assembly method according to embodiment one of the present disclosure.

(3) The sliding portion 320 may be pushed to drive the shaft 220 to move towards the distal end. The connecting end 230 may extend into the connecting hole 430 and extrude the limiting convex 410 to extend outward in the direction of the arrows illustrated in FIG. 21. The limiting convex 410 may pass through the limiting hole 121 and extend into the limiting concave 240 such that the sheath 210 may be connected to the connecting pipe 120. The shaft 220 may continue to be driven to move toward the distal end, the expanded portion 231 of the clamping portion may pass through the clamping hole 115, edges of the clamping hole 115 may buckle the recessed portion 232 such that the shaft 220 may be fixedly connected to the clip. At this time, as shown in FIG. 21, the clip may be driven to move towards the distal end or the proximal end by moving the shaft 220.

(4) The shaft 220 may be pulled to move towards the proximal end to drive the clip to move to the proximal end. The clip may gradually enter the connecting pipe 120 may be closed. At this time, the clip arms 110 may not prevent the clip from moving out of the chamber 511 for accommodating the clip. Then, as shown in FIG. 21, the shaft 220 can be continuously pulled towards the proximal end until the end effector device 100 and the delivery device 200 disengage from the opening of the proximal end of the chamber for accommodating the sheath 210 of the assembly box 500.

At this point, the assembly may be completed.

The chamber 511 for accommodating the clip may be open or not open. Preferably, from the viewpoint of sterilization, the end effector device 100 may be sealed in the chamber 511 for accommodating the clip before leaving the factory.

Embodiment Two

Figure 24:
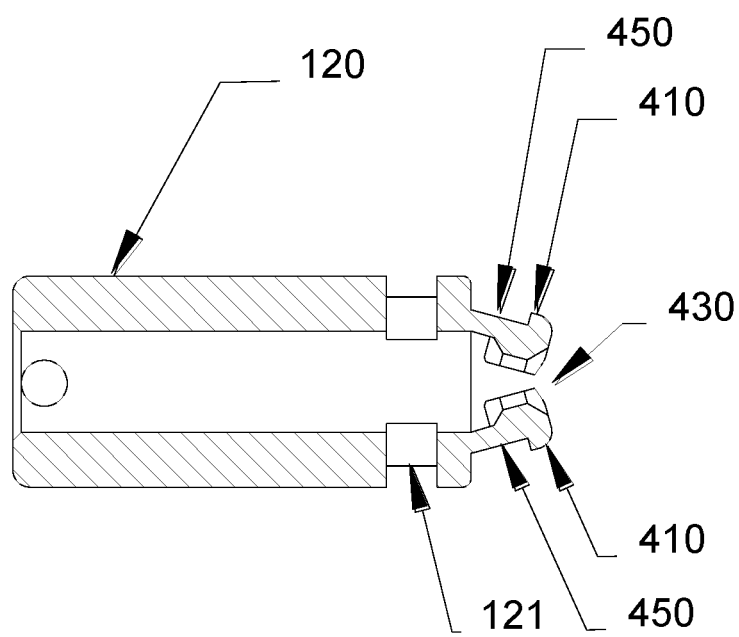
FIG. 24 is a schematic diagram illustrating a connecting pipe according to embodiment two of the present disclosure.
Figure 25:
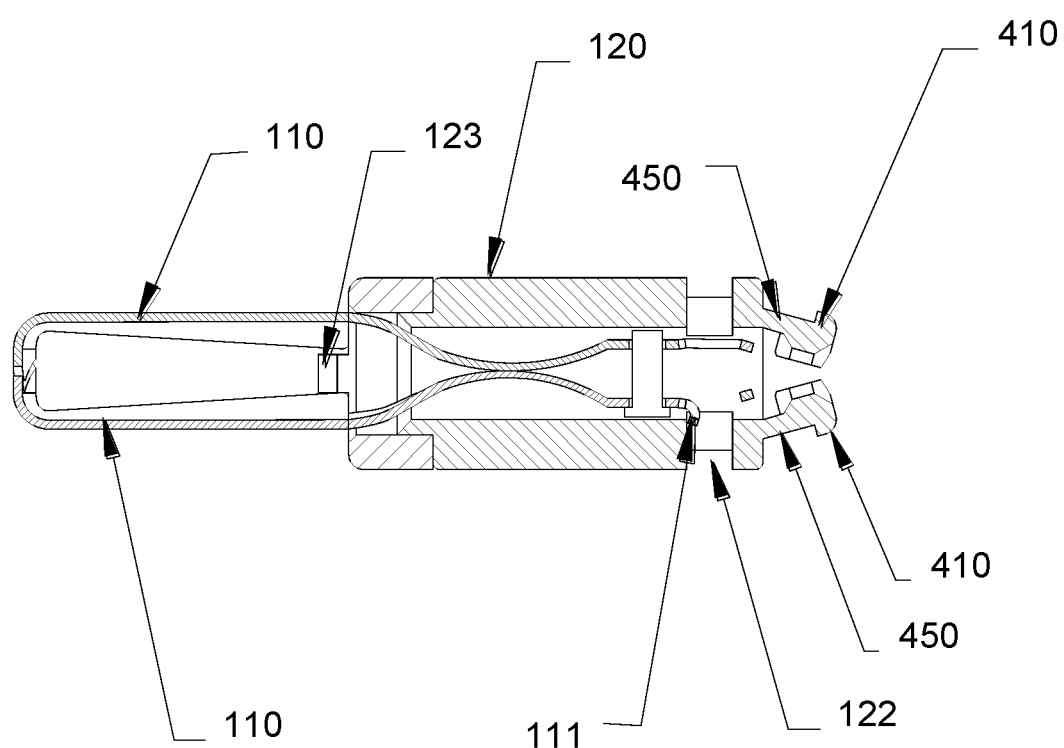
FIG. 25 is a schematic diagram illustrating a connecting pipe and a clip according to embodiment two of the present disclosure.
Figure 26:
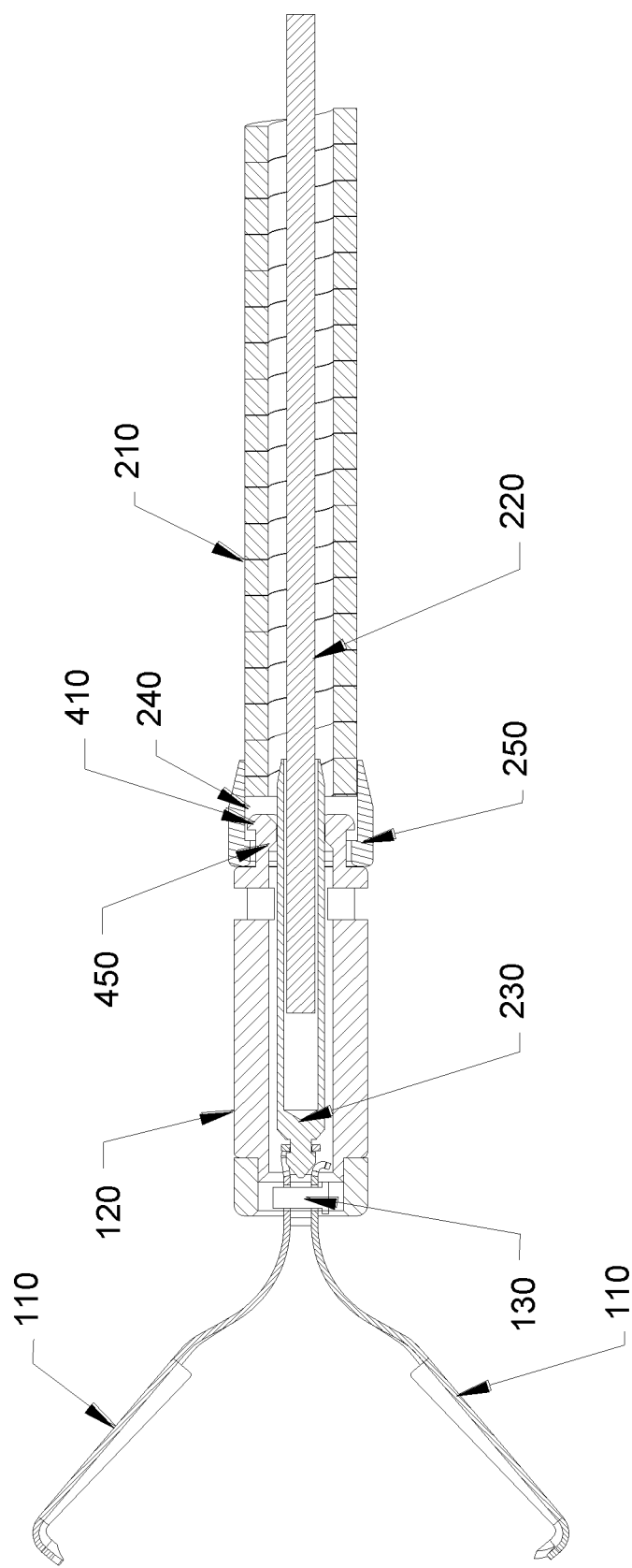
FIG. 26 is a schematic diagram illustrating an end effector device and a delivery device according to embodiment two of the present disclosure.

Differences between embodiment two and embodiment one may include:

As shown in FIGS. 24 to 26, the resilient portion 450 may be integrated with the connecting pipe 120. The connecting pipe 120 may be tubular. The resilient portion 450 may be fabricated on a pipe wall of the proximal end of the connecting pipe 120, and the channel of the connecting pipe 120 may coincide with the connecting hole 430. When the connecting end 230 extends into the connecting hole 430, the limiting convex 410 on the resilient portion 450 may be extruded outward into the limiting concave 240 of the sheath 210 such that the sheath 210 may be fixedly connected to the connecting pipe 120. When the connecting end 230 exits from the connecting hole 430, the resilient portion 450 may automatically rebound like a spring arm and cause the limiting convex 410 to exit from the limiting concave 240, and the connection between the connecting end 230 and the sheath 210 may be released.

In some embodiments, the assembly of the end effector device 100 and the delivery device 200 may be similar to those described in embodiment one, and the assembly box 500 of embodiment one may be applied.

Embodiment Three

Figure 27:
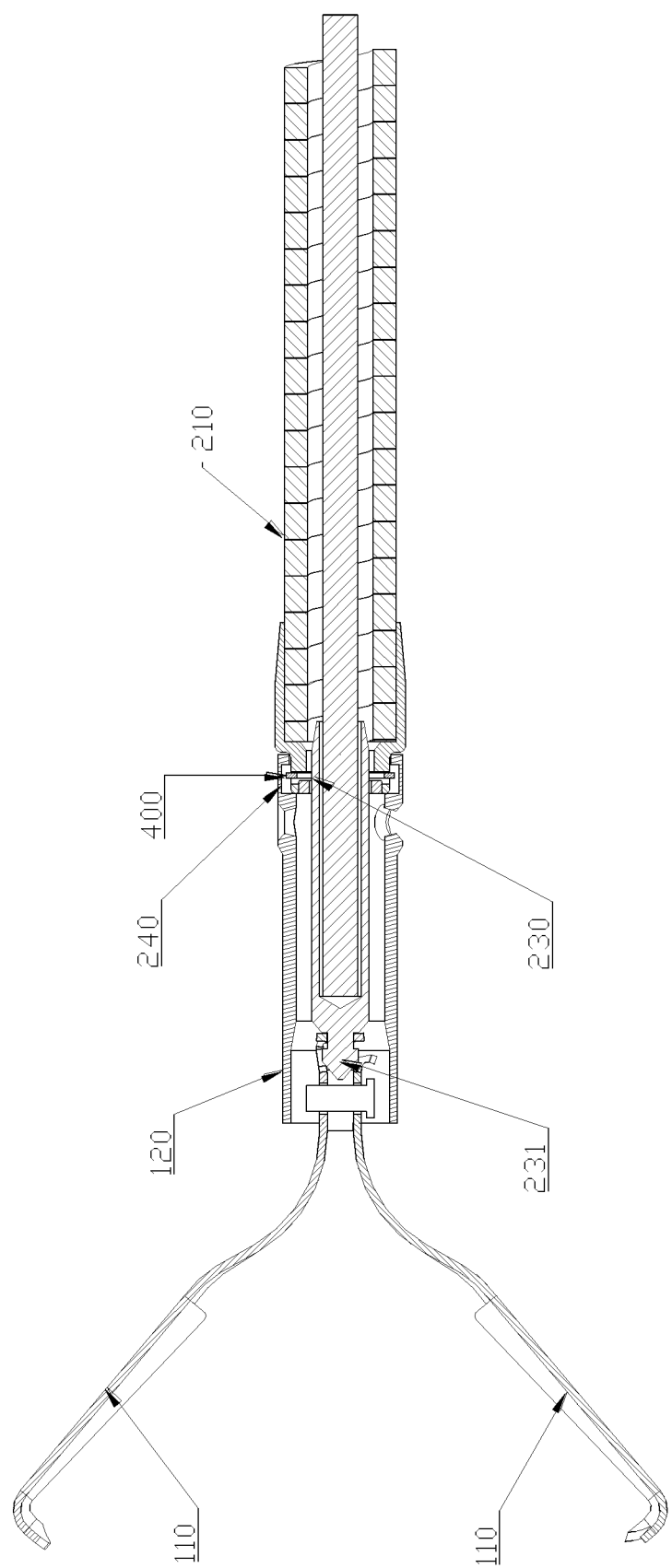
FIG. 27 is a schematic diagram illustrating an end effector device and a delivery device according to embodiment three of the present disclosure.
Figure 28:
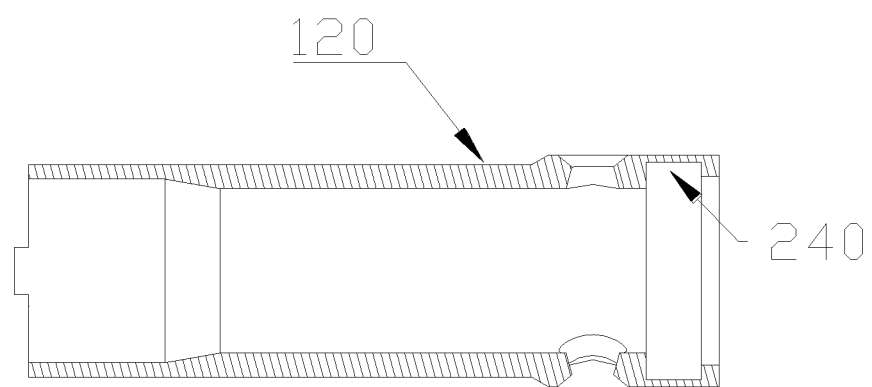
FIG. 28 is a schematic diagram illustrating a connecting pipe according to the embodiment three of the present disclosure.
Figure 29:
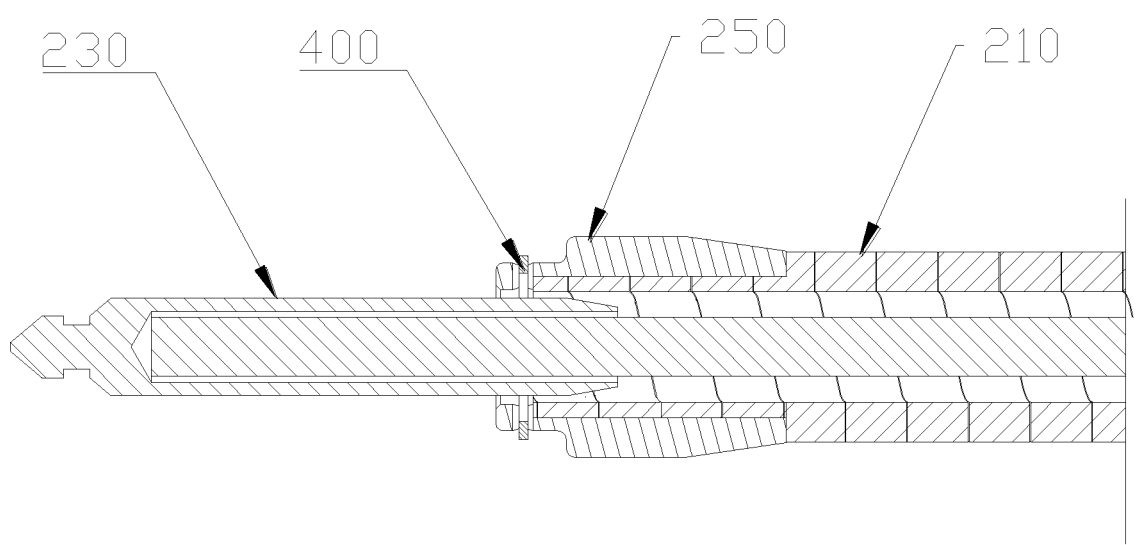
FIG. 29 is a schematic diagram illustrating a delivery device according to embodiment three of the present disclosure.

Differences between embodiment three and embodiment one may include:

Changes in positions of the resilient portion 450 and the limiting concave 240. As shown in FIGS. 27 to 29, the sheath 210 may include the resilient portion 450, and the connecting pipe 120 may include the limiting concave 240.

In some embodiments, the inner wall of the connecting pipe 120 may include the limiting concave 240.

The distal end of the sheath 210 may include an elastic ring 400. The elastic ring 400 may be set in the passage of the sheath 210. The elastic ring 400 may be the resilient portion, and the elastic ring 400 may include the connecting hole 430 and the limiting convex 410. The pipe wall of the sheath 210 may include a limiting hole 121 corresponding to the limiting convex 410.

When the elastic ring 400 extends into the channel of the connecting pipe 120, the connecting end 230 may extend into or exit from the connecting hole 430. When the connecting end 230 extends into the connecting hole 430, the elastic ring 400 may be extruded and expand outward, and the limiting convex 410 may extend into the limiting concave 240. When the connecting end 230 exits from the connecting hole 430, the elastic ring 400 may rebound, and the limiting convex 410 may exit from the limiting concave 240.

In some embodiments, the assembly of the end effector device 100 and the delivery device 200 may be similar to those described in embodiment one, and the assembly box 500 of embodiment one may be applied.

Embodiment Four

Figure 30:
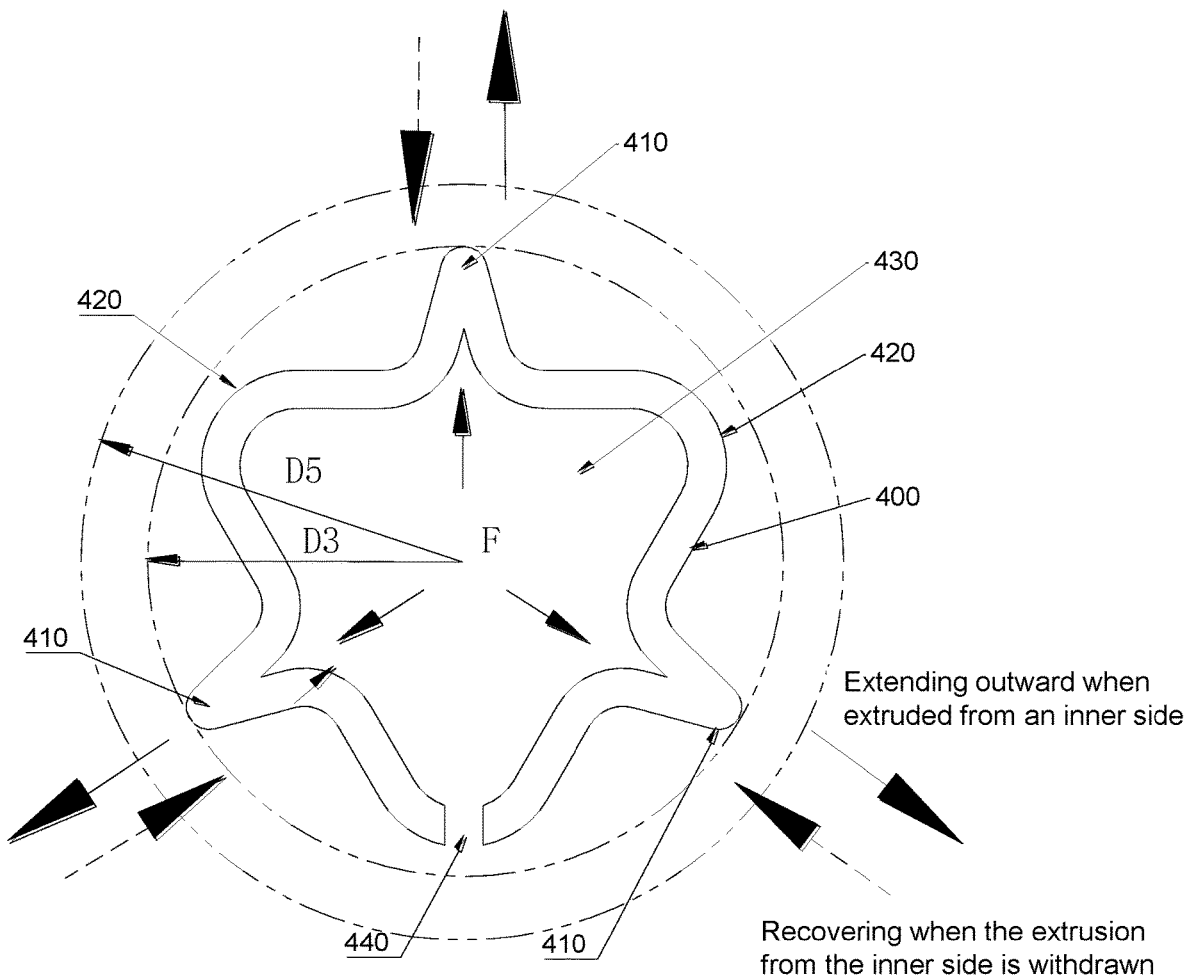
FIG. 30 is a schematic diagram illustrating an elastic ring according to embodiment four of the present disclosure.
Figure 31:
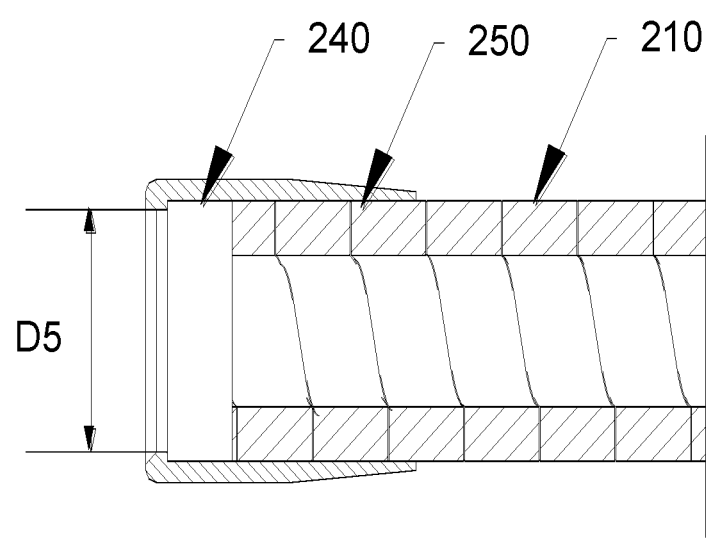
FIG. 31 is a schematic diagram illustrating a distal end of a sheath according to embodiment four of the present disclosure.

Differences between embodiment four and embodiment one may include:

Changes in the structure of the elastic ring 400. In some embodiments, the structure of the elastic ring 400 may change. In some embodiments, as shown in FIGS. 30 and 31, the elastic ring 400 may include the notch 440, and three limiting convexes 410 symmetrically arranged around the center. A protrusion between two adjacent limiting convexes 410 may form a limiting portion 420. The symmetrical distribution of the limiting convexes 410 may lead to a uniform distribution of forces on the elastic ring 400. The ring of the elastic ring 400 may protrude to form the limiting convexes 410, and may also protrude to form the limiting portion 420, thus having a simple structure.

When the connecting end is not inserted into the connecting hole, the diameter D3 formed by the three limiting convexes 410 may be smaller than the diameter D5 of the edge of the limiting concave distributed on the sheath, D3<D5, and the sheath may slide freely relative to the connecting pipe. When the connecting end is inserted into the connecting hole, the diameter formed by the three limiting convexes 410 may increase from D3 to D4, D4>D5, and the limiting convex may extend into the limiting concave, which limits the relative slide between the sheath and the connecting pipe.

Embodiment Five

Figure 32:
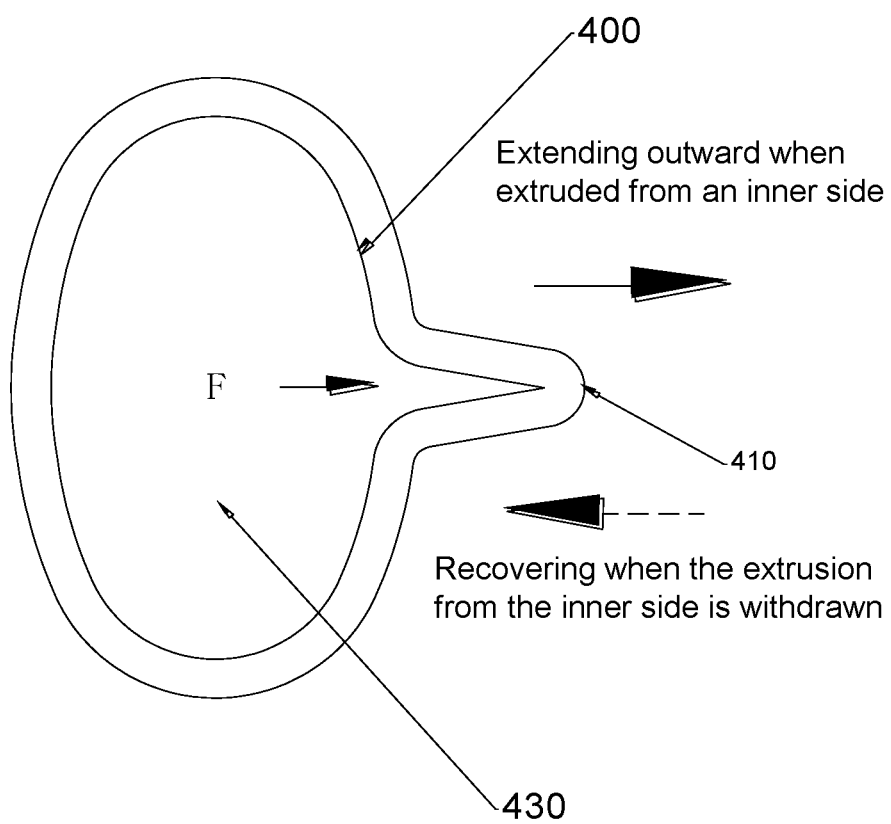
FIG. 32 is a schematic diagram 1 illustrating an elastic ring according to embodiment five of the present disclosure.

Differences between embodiment five and embodiment one may include:

Changes in the structure of the elastic ring 400. In some embodiments, as shown in FIG. 32, the limiting ring may be an ellipse, and the limiting convex 410 may be a convex stretching outward along the short axis of the ellipse. When the connecting end 230 is inserted into the limiting hole 121, the elastic ring 400 may be extruded outward along the short axis of the ellipse and in the direction of force F illustrated in FIG. 32, and the limiting convex 410 may expand outward. The limiting convex 410 may have a longer range for expanding outward and inward.

Figure 33:
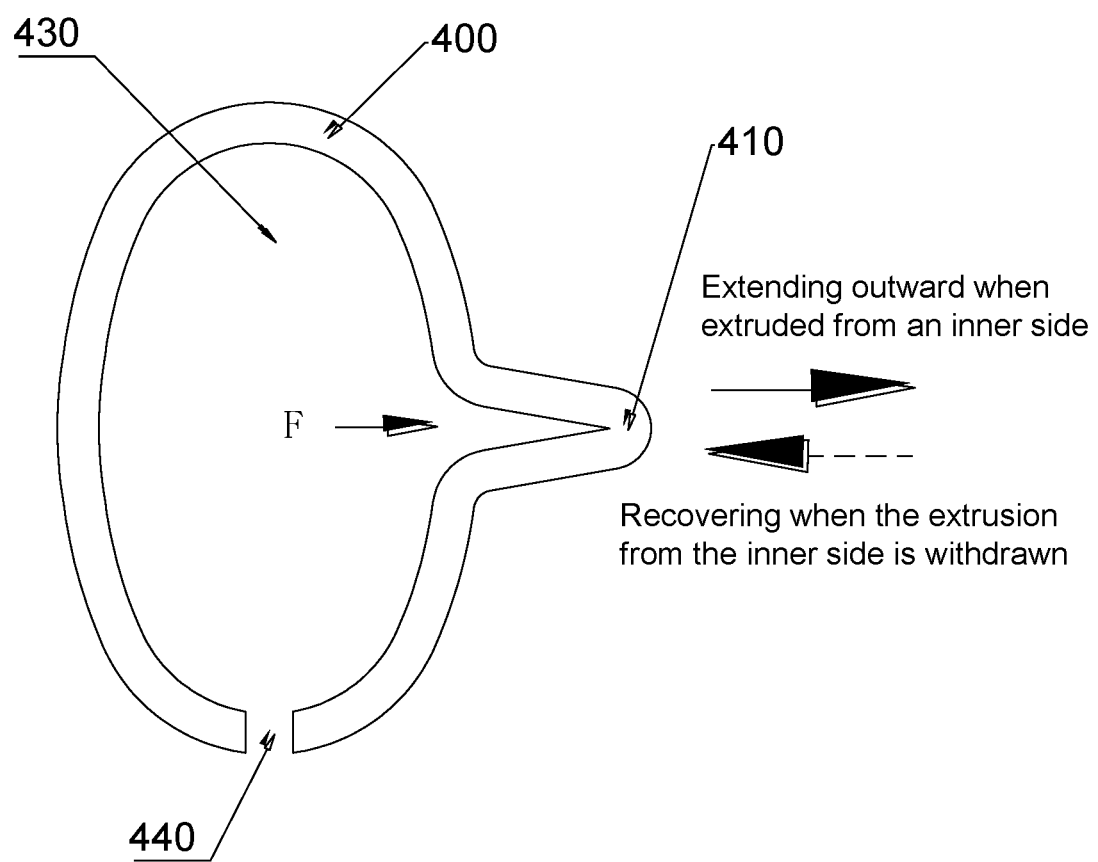
FIG. 33 is a schematic diagram 2 illustrating the elastic ring according to embodiment five of the present disclosure.
Figure 34:
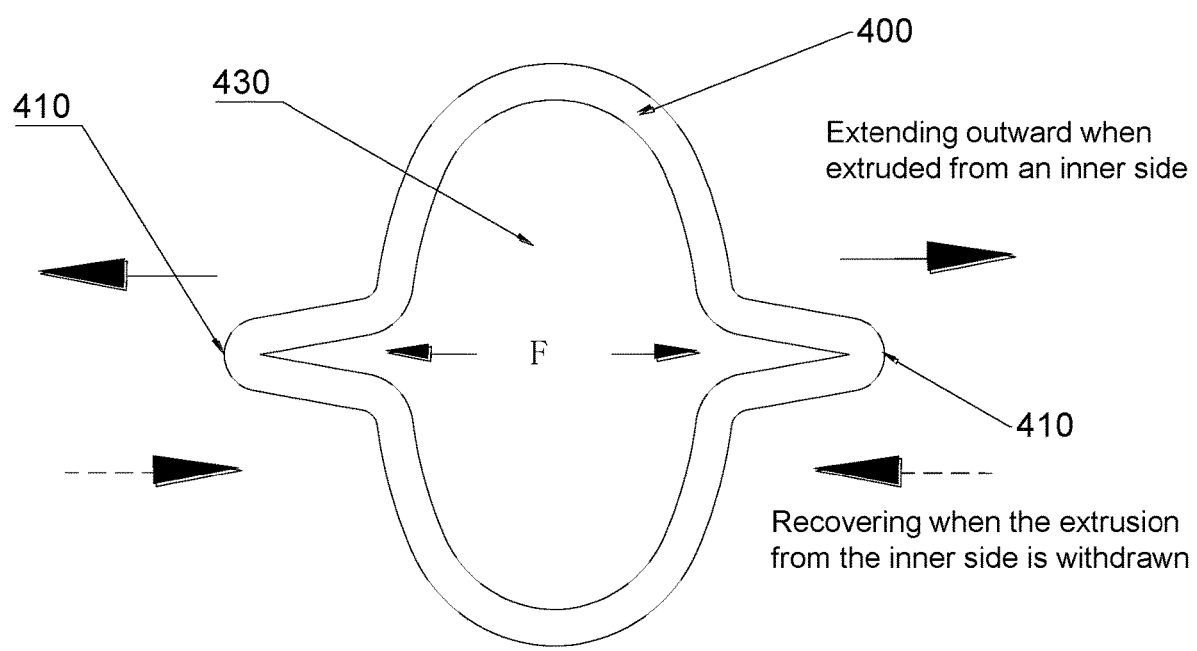
FIG. 34 is a schematic diagram 3 illustrating the elastic ring according to embodiment five of the present disclosure.
Figure 35:
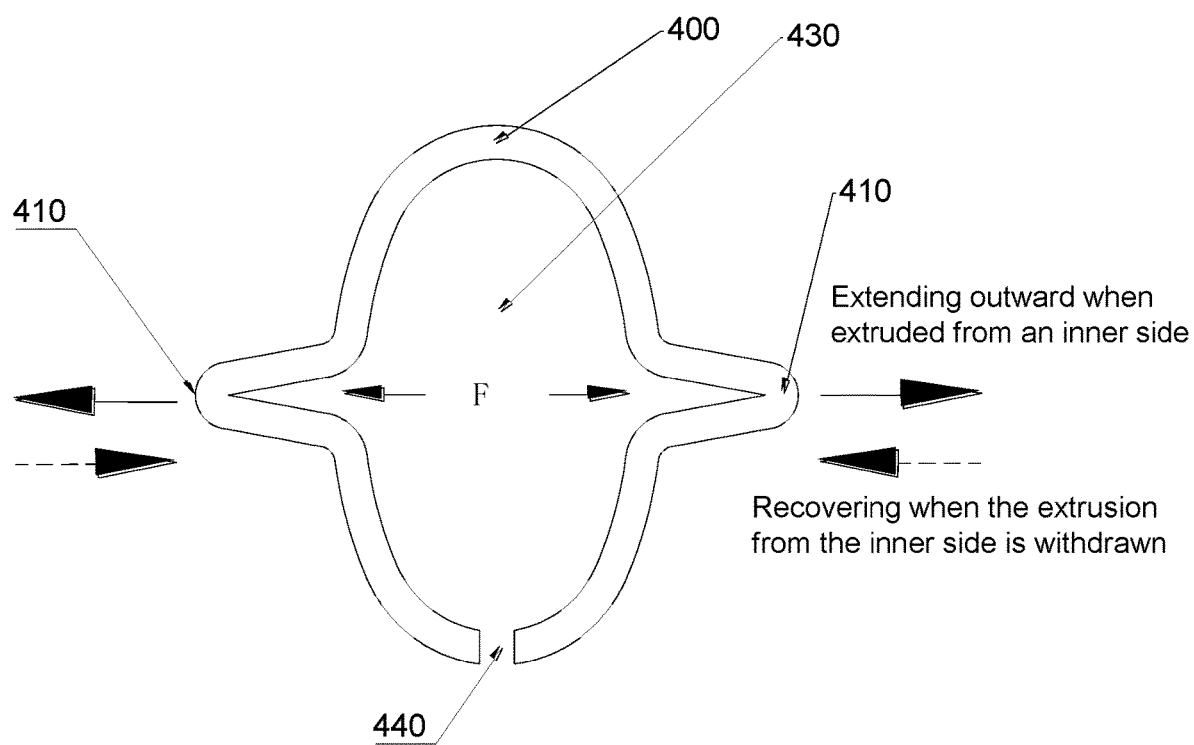
FIG. 35 is a schematic diagram 4 illustrating the elastic ring according to embodiment five of the present disclosure.

The limiting convex 410 may be set as shown in FIG. 32 and FIG. 33, or two limiting convexes 410 may also be set as shown in FIG. 34 and FIG. 35.

As shown in FIG. 33 and FIG. 35, the notch 440 may be set on the elastic ring 400. As shown in FIG. 32 and FIG. 34, the elastic ring 400 may also be a closed loop.

Embodiment Six

Figure 36:
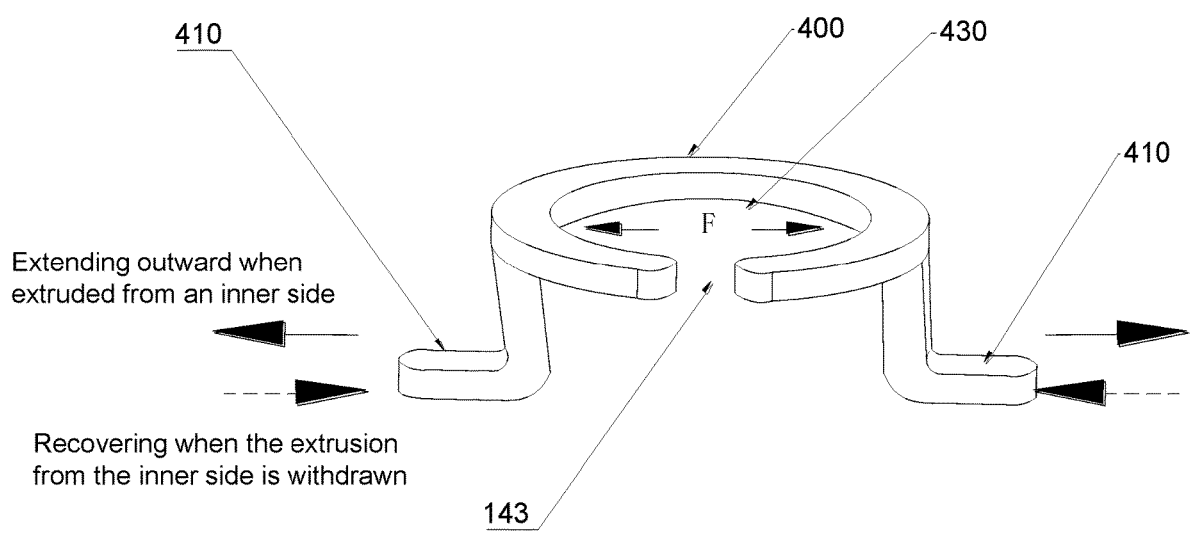
FIG. 36 is a schematic diagram illustrating an elastic ring according to embodiment six of the present disclosure.

Differences between embodiment six and embodiment one may include:

Changes in the structure of the elastic ring 400. In some embodiments, as shown in FIG. 36, the elastic ring 400 and the limiting convex 410 may not be on the same plane. One or more than two limiting convexes 410 may be set on the same side of the elastic ring 400.

Embodiment Seven

Figure 37:
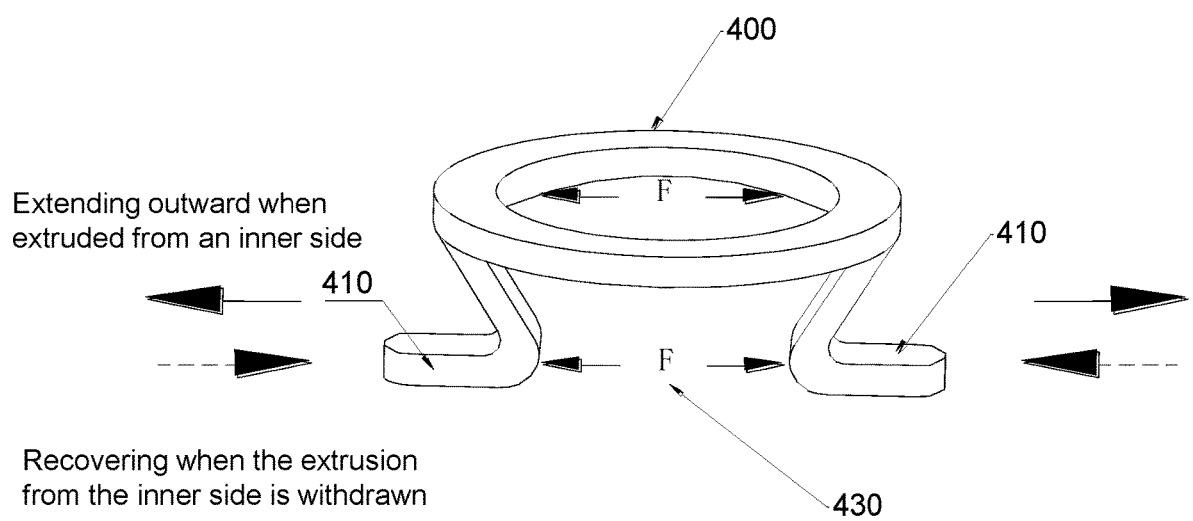
FIG. 37 is a schematic diagram illustrating an elastic ring according to embodiment seven of the present disclosure.

Differences between embodiment seven and embodiment one may include:

Changes in the structure of the elastic ring 400. In some embodiments, as shown in FIG. 37, one side of the elastic ring 400 may include two or more "J" hooks. One end of the "J" hook may be connected to the elastic ring 400, another end thereof may be a free end. The free end may form the limiting convex 410. When the connecting end 230 is inserted into the connecting hole 430, the connecting end 230 may simultaneously extrude the elastic ring 400 and the "J" hook, causing the limiting convex 410 to expand outward. When the connecting end 230 exits from the connecting hole 430, the elastic ring 400 and the "J" hook may rebound, causing the limiting convex 410 to rebound inward. The elastic ring 400 may be a circular ring, or an elliptical ring.

Embodiment Eight

Figure 38:
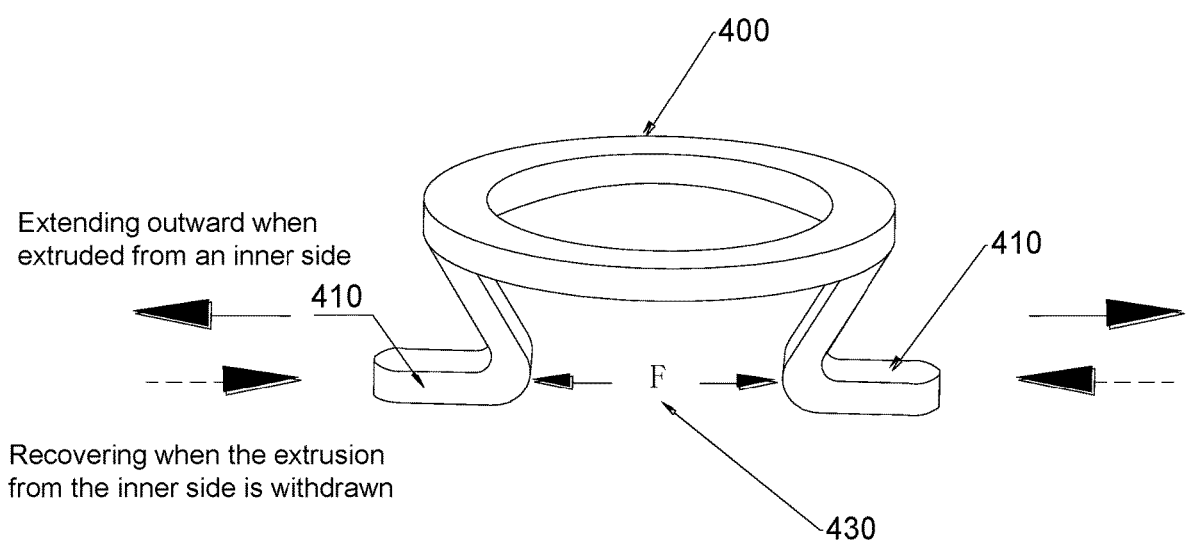
FIG. 38 is a schematic diagram 1 illustrating the elastic ring according to embodiment eight of the present disclosure.
Figure 39:
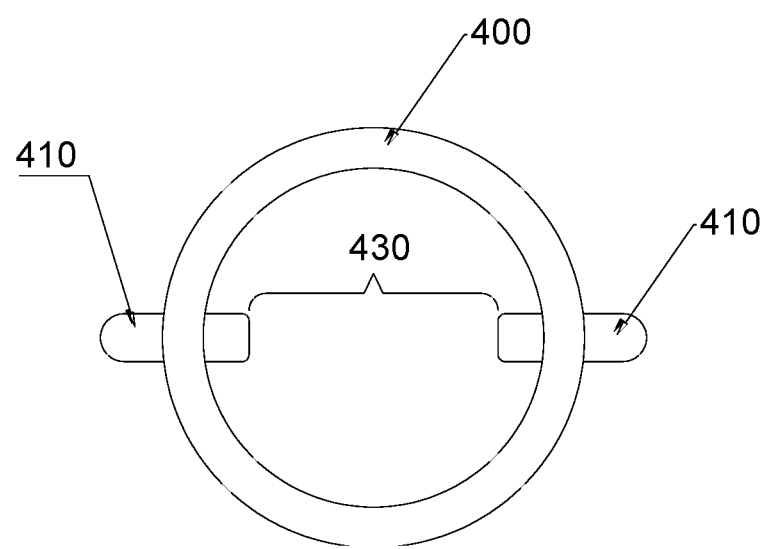
FIG. 39 is a schematic diagram 2 illustrating the elastic ring according to embodiment eight of the present disclosure.

Differences between Embodiment eight and Embodiment one may include:

As shown in FIGS. 38 and 39, the "J" hook may have an inward concave structure. The space between two "J" hooks may form the connecting hole 430. When the connecting end 230 is inserted into the connecting hole 430, the connecting end 230 may pass through but not extrude the elastic ring 400, and the connecting end 230 may extrude the "J" hooks to cause the limiting convex 410 to expand outward. When the connecting end 230 exits from the connecting hole 430, the "J" hooks may rebound and cause the limiting convex 410 to extend inward.

Embodiment Nine

Figure 40:
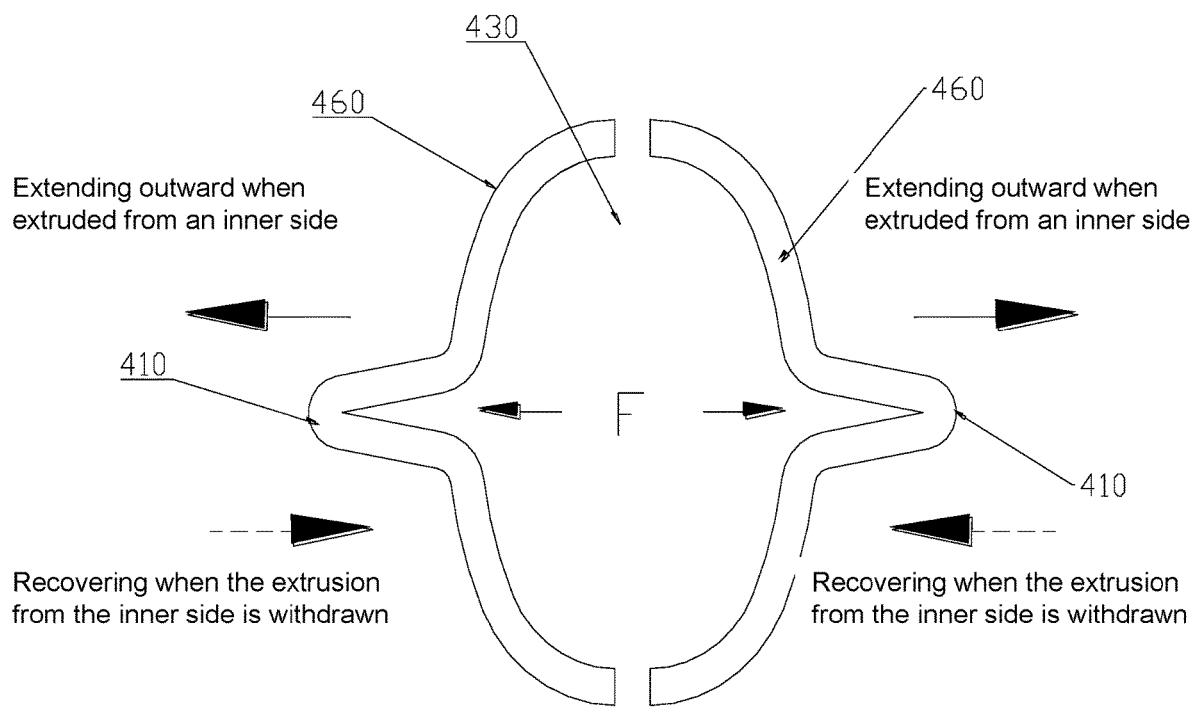
FIG. 40 is a schematic diagram illustrating an elastic ring according to embodiment nine of the present disclosure.

Differences between Embodiment nine and Embodiment one may include:

As shown in FIG. 40, the elastic ring 400 may include at least two half-rings 460. The at least two half-rings 460 may form the connecting hole 430. The half-ring 460 may include the limiting convex 410.

The half-ring 460 may be set directly within the channel of the connecting pipe 120 to align the limiting convex 410 with the limiting hole 121. The half-ring 460 may be a ½ ring, a ⅓ ring, or a ring of other shapes, as long as it may automatically rebound when the connecting end exits from the connecting hole 430, such that the connection between the end effector device 100 and the sheath 210 may be released.

Embodiment Ten

Difference between Embodiment ten and Embodiment nine may include:

The resilient portion may include a half-ring, referring to the half-ring on the left or the right of FIG. 40. The half-ring may be set in the channel of the connecting pipe. One side of the half-ring may include a limiting convex, and the other side of the half-ring may form a connecting hole with the inner wall of the connecting pipe.

Embodiment Eleven

Figure 41:
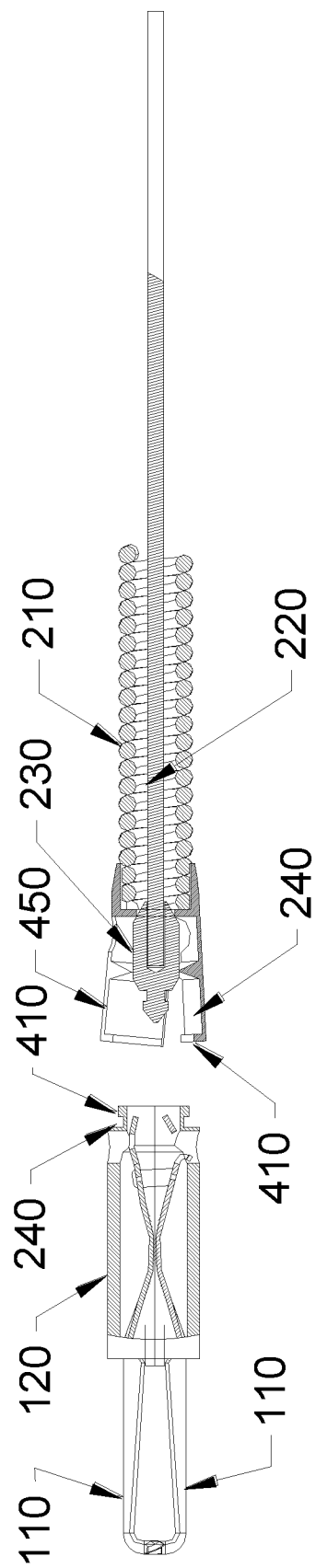
FIG. 41 is a schematic diagram illustrating a connecting pipe and a sheath in an unconnected state according to embodiment eleven of the present disclosure.
Figure 42:
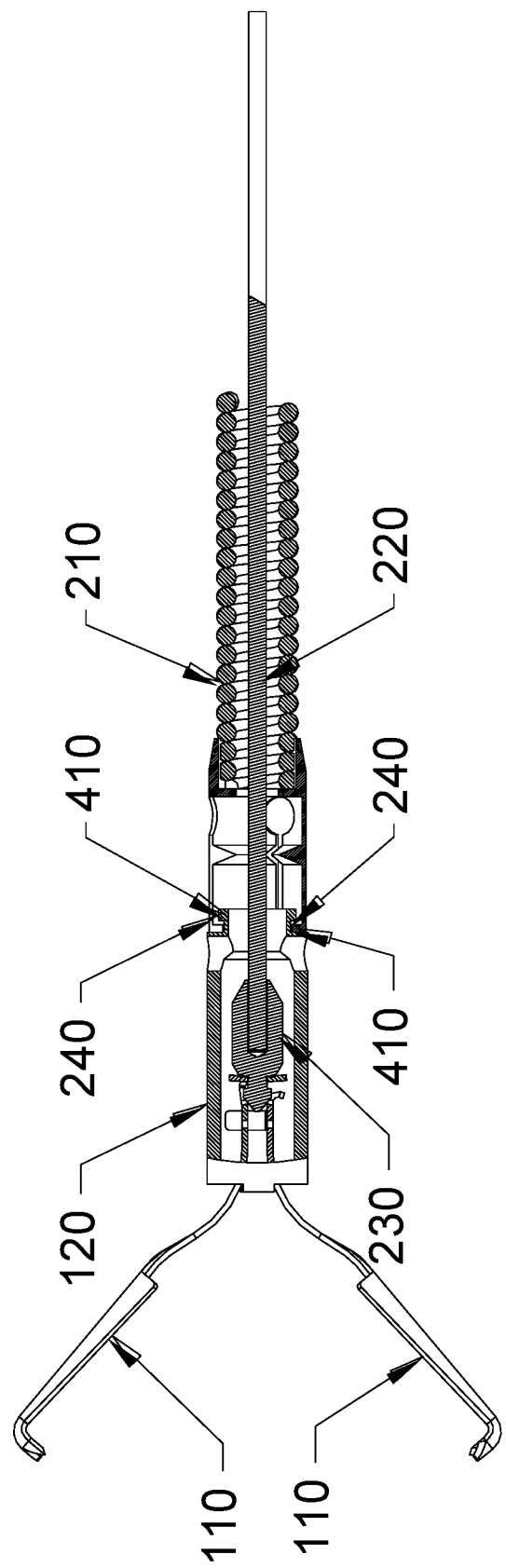
FIG. 42 is a schematic diagram illustrating a connecting pipe and a sheath in a connected state according to embodiment eleven of the present disclosure.

Differences between Embodiment eleven and Embodiment one may include:

As shown in FIGS. 41 and 42, the sheath 210 may include the resilient portion 450, and the resilient portion 450 may be integrated with the sheath 210 (or the resilient portion 450 and the sheath may be separated, which is not limited in this embodiment). The outer wall of the connecting pipe 120 may include the limiting concave 240, and the inner wall of the resilient portion 450 may include the limiting convex 410.

The resilient portion 450 may include the connecting hole 430. The connecting hole 430 may be connected to the passage of the sheath 210 to allow the connecting end 230 to move towards the distal end. When the connecting end 230 extends into the connecting hole 430, the limiting convex 410 of the resilient portion 450 may be extruded outward and thus open. The connecting hole 430 may allow the connecting pipe 120 and the limiting convex 410 to pass through, such that the proximal end of the connecting pipe 120 may extend into the connecting hole, and then the connecting end 230 may move towards the distal end. When the connecting end 230 passes through the connecting hole 430, the extrusion force applied by the connecting end 230 from the connecting hole 430 on the resilient portion 450 disappears, the resilient portion 450 may rebound, and the limiting convex 410 may extend into the limiting concave 240. The limiting convex 410 and the limiting concave 240 may cooperate to connect the connecting pipe 120 and the sheath 210. At this point, the end effector device may be driven to move by operating the delivery device 200. To release the connection between the connecting pipe 120 and the sheath 210, the connecting end 230 may be moved to the proximal end. When the connecting end 230 extends into the connecting hole 430, the connecting end 230 may apply an extrusion force from the inner wall of the connecting hole 430 to the resilient portion 450, the resilient portion 450 may be enlarged, and the connecting hole 430 may allow the connecting pipe 120 and the limiting convex 410 to pass through. At this point, the proximal end of the connecting pipe 120 may be separated from the distal end of the sheath 210, and the connection between the connecting pipe 120 and the sheath 210 may be released. Then the connecting end 230 may continue to move towards the proximal end. When the connecting end 230 exits from the connecting hole 430, the resilient portion 450 may rebound, and the sheath 210 and the resilient portion 450 may be ready to be connected to the connecting pipe 120 next time.

In some embodiments, the connecting pipe 120 may include the limiting condom 240 and the limiting convex 410. The resilient portion 450 may include the limiting concave 240 and the limiting convex 410. The limiting concave 240 and the limiting convex 410 may be buckled to form a connection. However, it is not limited thereto. The connecting pipe 120 may include the limiting concave 240, and the resilient portion 450 may include the limiting convex 410. Alternatively, the connecting pipe 120 may include the limiting convex 410, and the resilient portion 450 may include the limiting concave 240.

Embodiment Twelve

Figure 43:
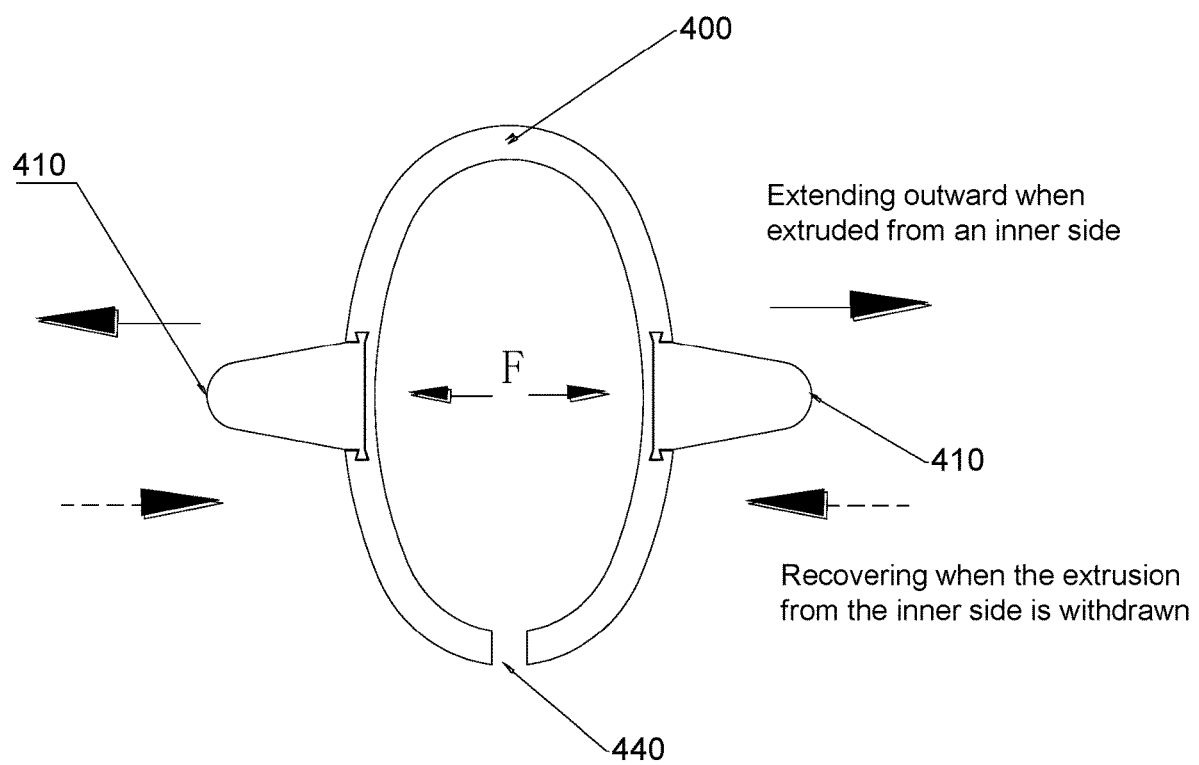
FIG. 43 is a schematic diagram illustrating an elastic ring according to embodiment twelve of the present disclosure.

Differences between embodiment twelve and embodiment five may include:

As shown in FIG. 43, the elastic ring 400 and the limiting convex 410 may be separated. The limiting convex 410 may be mounted on the elastic ring 400 by buckling, soldering, bonding or in other connection ways.

The technical features of the above embodiments may be arbitrarily combined. For brevity, all possible combinations of the various technical features in the above embodiments are not fully described. However, as long as there is no contradiction in the combination of these technical features, it should be considered as the scope of this specification.

The above embodiments are merely illustrative of several embodiments of the present disclosure, and the description thereof is specific and detailed, but is not to be construed as limiting the scope of the invention. It should be noted that, for those skilled in the art, there are several variations and modifications that may be made to the present disclosure without departing from the present disclosure concept. Therefore, the scope of protection of the present disclosure patent shall be subject to the appended claims.

What is claimed is:

1. A system, comprising:
a delivery device including a sheath and a shaft, the sheath providing a passage for accommodating the shaft, the shaft longitudinally movable relative to the sheath;
a clip assembly releasably coupled to a distal end of the delivery device, the clip assembly including a connecting pipe and a pair of clip arms that are slidably received within a channel of the connecting pipe; and
a resilient portion, the resilient portion having a hole to receive the shaft, the resilient portion changing between a first configuration, in which the shaft is received in the hole of the resilient portion such that the connecting pipe is fixedly coupled to the sheath, and a second configuration, in which the shaft is released from the hole of the resilient portion such that the connecting pipe is detached from the sheath.

2. The system of claim 1, wherein the resilient portion and the connecting pipe forms an integration structure, and the resilient portion is arranged at a proximal end of the integration structure.

3. The system of claim 1, wherein the resilient portion and the sheath forms an integration structure, and the resilient portion is arranged at a distal end of the integration structure.

4. The system of claim 1, wherein the resilient portion is detachably coupled to the connecting pipe or the sheath.

5. The system of claim 1, wherein the sheath includes a limiting concave, and the resilient portion includes a limiting convex, wherein the first configuration of the resilient portion causes the limiting convex to be received within the limiting concave, and the second configuration of the resilient portion causes the limiting convex to be out of the limiting concave.

6. The system of claim 5, wherein the resilient portion is an elastic ring that is disposed within the connecting pipe, and the connecting pipe includes a limiting hole through which the limiting convex of the elastic ring extends to the limiting concave of the sheath.

7. The system of claim 6, wherein the elastic ring includes a notch, and a dimension of the notch when the elastic ring is in its first configuration is different from a dimension of the notch when the elastic ring is in its second configuration.

8. The system of claim 1, wherein the connecting pipe includes a limiting concave, and the resilient portion includes a limiting convex, wherein the first configuration of the resilient portion causes the limiting convex to be received within the limiting concave, and the second configuration of the resilient portion causes the limiting convex to be out of the limiting concave.

9. The system of claim 8, wherein the resilient portion is an elastic ring that is disposed within the sheath, and the sheath includes a limiting hole through which the limiting convex of the elastic ring extends to the limiting concave of the connecting pipe.

10. The system of claim 1, wherein a centroid of the resilient portion changes when the resilient portion changes from the first configuration to the second configuration.

11. The system of claim 1, wherein the pair of clip arms forms a clamping hole at a proximal end thereof, and a size of the clamping hole varies when the pair of clip arms slide within the channel of the connecting pipe.

12. The system of claim 11, wherein the shaft includes a clamping portion at its distal end, and the clamping portion includes an expanded portion and a recessed portion, the expanded portion having a larger cross-section than that of the recessed portion.

13. The system of claim 12, wherein a maximum size of the cross-section of the expanded portion is larger than a minimum size of the clamping hole.

14. An end effector device, comprising:
- a clip assembly including a connecting pipe and a pair of clip arms that are slidably received within a channel of the connecting pipe; and
- a resilient portion coupled to the clip assembly, the resilient portion having a hole to receive a shaft of a delivery device, the resilient portion changing between a first configuration, in which the resilient portion receives the shaft and extends laterally outward relative to a longitudinal axis of the connecting pipe, and a second configuration, in which the shaft resilient portion releases the shaft and extends laterally inward relative to the longitudinal axis of the connecting pipe.

15. The end effector device of claim 14, wherein the resilient portion and the connecting pipe forms an integration structure, and the resilient portion is disposed at a proximal end of the integration structure.

16. The end effector device of claim 14, wherein the resilient portion is detachably coupled to the connecting pipe.

17. The end effector device of claim 14, wherein the resilient portion is an elastic ring that is disposed within the connecting pipe and has a limiting convex, and the connecting pipe includes a limiting hole through which the limiting convex of the elastic ring extends.

18. The end effector device of claim 14, wherein the pair of clip arms forms a clamping hole at a proximal end thereof, and a size of the clamping hole varies when the pair of clip arms slide within the channel of the connecting pipe.

\* \* \* \* \*